US007914775B2

(12) United States Patent
Cottard et al.

(10) Patent No.: US 7,914,775 B2
(45) Date of Patent: Mar. 29, 2011

(54) COMPOSITION FOR TREATING KERATINOUS MATERIALS COMPRISING A CATIONIC ASSOCIATIVE POLYURETHANE POLYMER AND A PROTECTING OR CONDITIONING AGENT

(75) Inventors: François Cottard, Levallois-Perret (FR); Roland De La Mettrie, Le Vesinet (FR)

(73) Assignee: L'Oreal S.A., Paris (FR)

( * ) Notice: Subject to any disclaimer, the term of this patent is extended or adjusted under 35 U.S.C. 154(b) by 1603 days.

(21) Appl. No.: 10/432,038

(22) PCT Filed: Nov. 6, 2001

(86) PCT No.: PCT/FR01/03426
§ 371 (c)(1),
(2), (4) Date: May 19, 2003

(87) PCT Pub. No.: WO02/39964
PCT Pub. Date: May 23, 2002

(65) Prior Publication Data
US 2004/0037796 A1    Feb. 26, 2004

(30) Foreign Application Priority Data
Nov. 20, 2000  (FR) ..................... 00 14949

(51) Int. Cl.
*A61Q 5/02*  (2006.01)
*A61Q 5/12*  (2006.01)
(52) U.S. Cl. ............... 424/70.9; 424/70.11; 424/70.122
(58) Field of Classification Search .................. None
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer |
| 2,781,354 A | 2/1957 | Mannheimer |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Matter et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 3,990,991 A * | 11/1976 | Gerstein ............ 510/124 |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,137,180 A | 1/1979 | Naik et al. |
| 4,165,367 A | 8/1979 | Chakrabarti |
| 4,166,894 A | 9/1979 | Schaper |
| 4,172,887 A | 10/1979 | Vanlerberghe et al. |
| 4,189,468 A | 2/1980 | Vanlerberghe et al. |
| 4,197,865 A | 4/1980 | Jacquet et al. |
| 4,223,009 A | 9/1980 | Chakrabarti |
| 4,240,450 A | 12/1980 | Grollier et al. |
| 4,277,581 A | 7/1981 | Vanlerberghe et al. |
| 4,349,532 A | 9/1982 | Vanlerberghe et al. |
| 4,381,919 A | 5/1983 | Jacquet et al. |
| 4,445,521 A | 5/1984 | Grollier et al. |
| 4,591,610 A | 5/1986 | Grollier |
| 4,608,250 A | 8/1986 | Jacquet et al. |
| 4,693,935 A | 9/1987 | Mazurek |
| 4,719,099 A | 1/1988 | Grollier et al. |
| 4,728,571 A | 3/1988 | Clemens et al. |
| 4,761,273 A | 8/1988 | Grollier et al. |
| 4,839,166 A | 6/1989 | Grollier et al. |
| 4,874,554 A | 10/1989 | Lange et al. |
| 4,972,037 A | 11/1990 | Garbe et al. |

(Continued)

FOREIGN PATENT DOCUMENTS
EP    0 122 324 A1    10/1984
(Continued)

OTHER PUBLICATIONS

English language esp@cenet abstract of DE 44 02 929. English language esp@cenet abstract of DE 44 20 736.
English language esp@cenet abstract of DE 44 24 530.
English language esp@cenet abstract of DE 44 24 533.
English language esp@cenet abstract of EP 0 080 976.
English language DERWENT abstract of FR 2 673 839.
English language DERWENT abstract of FR 2 589 476.
English language DERWENT abstract of FR 2 336 434.
PCT Search Report for present application.
P.D. Dorgan "Waxes in Cosmetics", Drug and Cosmetic Industry, Dec. 1983, pp. 30-33.
Porter, M.R., Handbook of Surfactants 116-178 (Blackie & Son 1991).
"Volatile Silicone Fluids for Cosmetic Formulations", Cosmetics and Toiletries, vol. 91, Jan. 1976, pp. 27-32.

(Continued)

*Primary Examiner* — Jyothsna A Venkat
(74) *Attorney, Agent, or Firm* — Finnegan, Henderson, Farabow, Garrett & Dunner

(57) ABSTRACT

The invention concerns a composition for treating keratinous fibers, in particular human keratinous fibers such as hair, comprising in a physiologically acceptable medium, at least a protecting or conditioning agent, and further at least a cationic associative polyurethane polymer. The invention also concerns methods and devices using said composition.

43 Claims, No Drawings

U.S. PATENT DOCUMENTS

| | | | |
|---|---|---|---|
| 4,996,059 A | | 2/1991 | Grollier et al. |
| 5,009,880 A | | 4/1991 | Grollier et al. |
| 5,089,252 A | | 2/1992 | Grollier et al. |
| 5,227,153 A | | 7/1993 | Grollier et al. |
| 5,240,695 A | | 8/1993 | Dubief et al. |
| 5,369,857 A | * | 12/1994 | Sacherman et al. ............ 29/594 |
| 5,443,840 A | * | 8/1995 | Morancais et al. ........... 424/450 |
| 5,616,746 A | | 4/1997 | Mahieu et al. |
| 5,618,523 A | | 4/1997 | Zysman et al. |
| 5,773,611 A | | 6/1998 | Zysman et al. |
| 5,807,957 A | * | 9/1998 | Samour et al. .................. 528/49 |
| 6,001,376 A | | 12/1999 | Mahieu et al. |
| 6,210,691 B1 | | 4/2001 | Mahieu et al. |
| 6,221,817 B1 | * | 4/2001 | Guskey et al. ................ 510/122 |
| 7,077,869 B2 | | 7/2006 | Legrand et al. |
| 2002/0119113 A1 | * | 8/2002 | Ellis et al. .................. 424/70.22 |
| 2003/0124079 A1 | * | 7/2003 | Mougin et al. ............. 424/70.11 |

FOREIGN PATENT DOCUMENTS

| | | |
|---|---|---|
| EP | 0 186 507 A2 | 7/1986 |
| EP | 0 227 994 A1 | 7/1987 |
| EP | 0 337 354 A1 | 10/1989 |
| EP | 0 342 834 A2 | 11/1989 |
| EP | 0 412 704 A2 | 2/1991 |
| EP | 0 412 707 A1 | 2/1991 |
| EP | 0 486 135 A2 | 5/1992 |
| EP | 0 582 152 A2 | 2/1994 |
| EP | 0 646 572 A1 | 4/1995 |
| WO | WO 93 23009 | 11/1993 |
| WO | WO 93/23446 | 11/1993 |
| WO | WO 94/07844 | 4/1994 |
| WO | WO 95/00578 | 1/1995 |
| WO | WO 95/16665 | 6/1995 |
| WO | WO 95/23807 | 9/1995 |

* cited by examiner

COMPOSITION FOR TREATING KERATINOUS MATERIALS COMPRISING A CATIONIC ASSOCIATIVE POLYURETHANE POLYMER AND A PROTECTING OR CONDITIONING AGENT

The invention relates to a composition for treating keratin materials, in particular human keratin fibers such as the hair, comprising, in a physiologically and in particular a cosmetically acceptable medium, at least one protecting or conditioning agent, and also at least one particular cationic associative polyurethane polymer.

The deposition of the protecting or conditioning agent for keratin fibers and the cosmetic properties may be improved with these combinations.

It is well known that the hair is sensitized or embrittled to varying degrees by the action of atmospheric agents and especially light, water and humidity, and also by the repeated action of various hair treatments such as washing, permanent-waving, straightening, dyeing and bleaching. Many publications disclose that natural light destroys certain amino acids of the hair. These attacks impair the hair fibers and reduce their mechanical properties, for instance the tensile strength, the breaking load and the elasticity, or their resistance to swelling in an aqueous medium. The hair then becomes dull, coarse and brittle. In contrast with the skin, the color of the hair becomes lighter.

It is also known that light and washing agents, especially, have a tendency to attack the natural color of the hair and also the artificial color of dyed hair. The color of the hair gradually fades or turns to unattractive or undesirable shades.

Substances for protecting the hair against the degradation caused by atmospheric attacking factors, such as light, heat and treatments, have been sought for many years in the cosmetics industry. In particular, products that protect the color of naturally colored or artificially dyed keratin fibers and that preserve or reinforce the intrinsic mechanical properties of keratin fibers (the tensile strength, the breaking load and the elasticity, or their resistance to swelling in an aqueous medium) are particularly sought.

It has already been proposed to use certain substances capable of screening out light radiation, for instance 2-hydroxy-4-methoxybenzophenone-5-sulfonic acid or its salts (FR-A-2 627 085), 4-(2-oxo-3-bornylidenemethyl)benzenesulfonic acid or its salts (EP-A-329 032) or lactoferrin (FR-A-2 673 839), to combat this degradation of hair keratin.

However, these screening agents, when they are effective, are only effective in large concentrations. At these concentrations though, hair treated with these screening agents has a coarse, heavy feel. Furthermore, it is extremely difficult to disentangle.

It has already been recommended, in compositions for washing or caring for keratin materials such as the hair, to use conditioners, especially cationic polymers or silicones, to facilitate the disentangling of the hair and to give it softness and suppleness. However, the cosmetic advantages mentioned above are unfortunately also accompanied, on dried hair, by certain cosmetic effects considered undesirable, i.e. lankness of the hairstyle (lack of lightness of the hair) and lack of smoothness (hair that is not uniform from the root to the end).

In addition, the use of cationic polymers with this aim presents various drawbacks. On account of their high affinity for the hair, some of these polymers become deposited to a substantial amount during repeated use, and lead to undesirable effects such as an unpleasant, heavy feel, stiffening of the hair and adhesion between the fibers that affects the styling.

These drawbacks are accentuated in the case of fine hair that lacks liveliness and body.

It is well known that hair that has been sensitized (i.e. damaged and/or embrittled) to varying degrees due to the action of atmospheric agents or due to the action of mechanical or chemical treatments, such as dyeing, bleaching and/or permanent-waving operations, is often difficult to disentangle and to style, and lacks softness.

In summary, it is found that the current cosmetic compositions containing protecting or conditioning agents are not entirely satisfactory.

The Applicant has now discovered that the combination of a particular cationic associative polyurethane with protecting or conditioning agents allows these drawbacks to be overcome.

Thus, after considerable research conducted in this matter, it has now been found by the Applicant that by introducing a particular polymer into compositions, in particular hair compositions based on protecting or conditioning agents for keratin materials, it is possible to increase the deposition of the protecting or conditioning agent for keratin materials and thereby to increase the protection or conditioning.

Furthermore, the distribution of the compositions during application to the keratin materials is easier and takes place more uniformly. The deposit is more uniform, as is the efficacy.

Without wishing to limit the present invention to any theory, it is believed that, during rinsing, there are particular interactions and/or affinities between the protecting or conditioning agent for keratin materials, the polyurethane polymers in accordance with the invention and the hair, which promote a uniform, substantial and long-lasting deposition of said protecting or conditioning agents for keratin materials and polyurethanes at the surface of said hair, this qualitative and quantitative deposition probably being one of the causes of the observed improvement in the final properties, in particular the ease of styling, the hold, the liveliness and the body of the treated hair.

All these discoveries form the basis of the present invention.

Thus, according to the present invention, novel cosmetic compositions are now proposed, comprising, in a physiologically and in particular a cosmetically acceptable medium, at least one protecting or conditioning agent for keratin materials and at least one cationic associative polyurethane of formula (I) below, with the exclusion of compositions for the direct dyeing of keratin fibers, comprising, in a medium that is suitable for dyeing, at least one direct dye and at least one cationic associative polyurethane of formula (I), with the exclusion of compositions for the oxidation dyeing of keratin fibers, comprising, in a medium that is suitable for dyeing, at least one oxidation dye and at least one cationic associative polyurethane of formula (I), with the exclusion of ready-to-use compositions for bleaching keratin fibers, comprising, in a medium that is suitable for bleaching, at least one oxidizing agent and at least one cationic associative polyurethane of formula (I), with the exclusion of ready-to-use compositions for bleaching or permanently reshaping keratin fibers, comprising, in a medium that is suitable for bleaching, at least one reducing agent and at least one cationic associative polyurethane of formula (I).

Another subject of the invention relates to the use of at least one cationic associative polyurethane of formula (I) in or for the manufacture of a cosmetic composition comprising a protecting or conditioning agent for keratin materials.

A subject of the invention is also the use of at least one cationic associative polyurethane of formula (I) in a cosmetic composition comprising a protecting agent for keratin materials, to increase the efficacy of this protecting or conditioning agent for keratin materials.

A subject of the present invention is also the use of at least one cationic associative polyurethane of formula (I) in a cosmetic composition comprising a protecting or conditioning agent for keratin materials, to improve the deposition and/or fixing of said protecting agent to the keratin materials.

The various subjects of the invention will now be presented in detail. All the meanings and definitions of the compounds used in the present invention given hereinbelow are valid for all the subjects of the invention.

Polymers capable of reversibly combining together or with other molecules for thickening are known as "associative polymers". This physical combination gives rise to thixotropic or shear-thinning macromolecular systems, i.e. systems whose viscosity depends on the shear forces to which they are subjected.

The forces of interaction involved may be of very different nature, for example of electrostatic nature, of hydrogen bonding type, or hydrophobic interactions.

One particular case of associative polymers is amphiphilic polymers, i.e. polymers comprising one or more hydrophilic portions that make them water-soluble, and one or more hydrophobic zones via which the polymers interact and assemble together or with other molecules.

Their chemical structure comprises at least one hydrophilic zone and at least one hydrophobic zone, the hydrophobic zone(s) comprising at least one fatty chain especially containing at least 10 carbon atoms and preferably from 10 to 30 carbon atoms.

The family of cationic amphiphilic associative polymers in accordance with the invention is represented by the general formula (I) below:

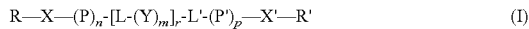

R—X—(P)$_n$-[L-(Y)$_m$]$_r$-L'-(P')$_p$—X'—R'  (I)

in which:

R and R', which may be identical or different, represent a hydrophobic group or a hydrogen atom;

X and X', which may be identical or different, represent a group comprising an amine function optionally bearing a hydrophobic group, or alternatively a group L";

L, L' and L", which may be identical or different, represent a group derived from a diisocyanate;

P and P', which may be identical or different, represent a group comprising an amine function optionally bearing a hydrophobic group;

Y represents a hydrophilic group;

r is an integer between 1 and 100, preferably between 1 and 50 and in particular between 1 and 25, n, m and p each range, independently of each other, from 0 to 1000;

the molecule containing at least one protonated or quaternized amine function and at least one hydrophobic group.

In one preferred embodiment of the polyurethanes of the present invention, the only hydrophobic groups are the groups R and R' at the chain ends.

One preferred family of cationic associative polyurethanes according to the present invention is the one corresponding to formula (I) above in which:

R and R' both independently represent a hydrophobic group,

X and X' each represent a group L", n and p are between 1 and 1000, and

L, L', L", P, P', Y and m have the meaning given above.

Another preferred family of cationic associative polyurethanes according to the present invention is the one corresponding to formula (I) above in which R and R' both independently represent a hydrophobic group, X and X' each represent a group L", n and p are 0, and L, L', L", Y and m have the meaning given above.

The fact that n and p are 0 means that these polymers do not comprise units derived from a monomer containing an amine function, incorporated into the polymer during the polycondensation. The protonated amine functions of these polyurethanes result from the hydrolysis of excess isocyanate functions, at the chain end, followed by alkylation of the primary amine functions formed with alkylating agents containing a hydrophobic group, i.e. compounds of the type RQ or R'Q, in which R and R' are as defined above and Q denotes a leaving group such as a halide, a sulfate, etc.

Yet another preferred family of cationic associative polyurethanes according to the present invention is the one corresponding to formula (I) above in which:

R and R' both independently represent a hydrophobic group,

X and X' both independently represent a group comprising a quaternary amine, n and p are zero, and L, L', Y and m have the meaning given above.

The number-average molecular mass of the cationic amphiphilic associative polyurethanes of the invention is preferably between 400 and 500 000, in particular between 1000 and 400 000 and ideally between 1000 and 300 000.

The expression "hydrophobic group" means a radical or polymer containing a saturated or unsaturated, linear or branched hydrocarbon-based chain, which may contain one or more hetero atoms such as P, O, N or S, or a radical containing a perfluoro or silicone chain. When the hydrophobic group denotes a hydrocarbon-based radical, it comprises at least 10 carbon atoms, preferably from 10 to 30 carbon atoms, in particular from 12 to 30 carbon atoms and more preferably from 18 to 30 carbon atoms.

Preferentially, the hydrocarbon-based hydrophobic group is derived from a monofunctional compound.

By way of example, the hydrophobic group may be derived from a fatty alcohol such as stearyl alcohol, dodecyl alcohol or decyl alcohol. The hydrophobic group may also be a hydrocarbon-based polymer such as, for example, polybutadiene.

When X and/or X' denote(s) a group comprising a tertiary or quaternary amine, X and/or X' may represent one of the following formulae:

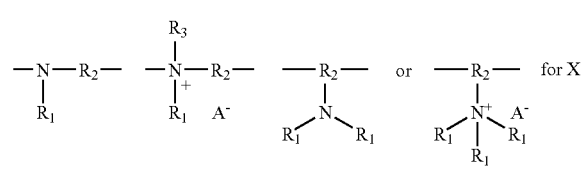

-continued $$-R_2-N(R_1)(R_3)- \quad -R_2-\overset{R_3}{\underset{R_1}{N^+}}-A^- \quad -R_2-\underset{\underset{R_1}{N}}{\overset{\phantom{R}}{\phantom{|}}}\phantom{-}-R_1 \quad or \quad -R_2-\underset{R_1}{\overset{R_1}{N^+}}-R_1 \; A^- \quad for \; X'$$

in which:
$R_2$ represents a linear or branched alkylene radical containing from 1 to 20 carbon atoms, optionally comprising a saturated or unsaturated ring, or an arylene radical, one or more of the carbon atoms possibly being replaced with a hetero atom chosen from N, S, O and P;
$R_1$ and $R_3$, which may be identical or different, denote a linear or branched $C_1$-$C_{30}$ alkyl or alkenyl radical or an aryl radical, at least one of the carbon atoms possibly being replaced with a hetero atom chosen from N, S, O and P;
$A^-$ is a physiologically acceptable counterion.

The groups L, L' and L'' represent a group of formula:

$$-Z-\underset{O}{\overset{\phantom{|}}{C}}-NH-R_4-NH-\underset{O}{\overset{\phantom{|}}{C}}-Z-$$

in which:
Z represents —O—, —S— or —NH—; and
$R_4$ represents a linear or branched alkylene radical containing from 1 to 20 carbon atoms, optionally comprising a saturated or unsaturated ring, or an arylene radical, one or more of the carbon atoms possibly being replaced with a hetero atom chosen from N, S, O and P.

The groups P and P' comprising an amine function may represent at least one of the following formulae:

$$-R_5-N(R_6)-R_7- \quad or \quad -R_5-\overset{R_8}{\underset{R_6}{N^+}}-R_7- \; A^- \quad or$$

$$-R_5-\underset{\underset{R_7}{CH}}{\overset{N(R_6)(R_8)}{\phantom{|}}}- \quad or \quad -R_5-CH(R_7)-\overset{R_8}{\underset{R_6}{N^+}}-R_9 \; A^- \quad or$$

$$-R_5-\underset{\underset{R_7}{CH}}{\overset{N(R_6)(R_8)}{\phantom{|}}}-R_{10} \quad or \quad -R_5-CH(R_7)(R_{10})-\overset{R_8}{\underset{R_6}{N^+}}-R_9 \; A^-$$

in which:
$R_5$ and $R_7$ have the same meanings as $R_2$ defined above;
$R_6$, $R_8$ and $R_9$ have the same meanings as $R_1$ and $R_3$ defined above;
$R_{10}$ represents a linear or branched, optionally unsaturated alkylene group possibly containing one or more hetero atoms chosen from N, O, S and P,
and $A^-$ is a physiologically acceptable counterion.

As regards the meaning of Y, the term "hydrophilic group" means a polymeric or nonpolymeric water-soluble group.

By way of example, when it is not a polymer, mention may be made of ethylene glycol, diethylene glycol and propylene glycol.

When it is a hydrophilic polymer, in accordance with one preferred embodiment, mention may be made, for example, of polyethers, sulfonated polyesters, sulfonated polyamides or a mixture of these polymers. The hydrophilic compound is preferentially a polyether and in particular a poly(ethylene oxide) or poly(propylene oxide).

The cationic associative amphiphilic polyurethanes of formula (I) according to the invention are formed from diisocyanates and from various compounds with functions containing a labile hydrogen. The functions containing a labile hydrogen may be alcohol, primary or secondary amine or thiol functions, giving, after reaction with the diisocyanate functions, polyurethanes, polyureas and polythioureas, respectively. The term "polyurethanes" chosen to denote the novel associative polymers of the present invention encompasses these three types of polymer, namely polyurethanes per se, polyureas and polythioureas, and also copolymers thereof.

A first type of compound involved in the preparation of the polymer of formula (I) of the invention is a compound comprising at least one unit containing an amine function. This compound may be multifunctional, but the compound is preferentially difunctional, that is to say that, according to one preferential embodiment of the invention, this compound comprises two labile hydrogen atoms borne, for example, by a hydroxyl, primary amine, secondary amine or thiol function. A mixture of multifunctional and difunctional compounds in which the percentage of multifunctional compounds is low may also be used.

As mentioned above, this compound may comprise more than one unit containing an amine function. In this case, it is a polymer bearing a repetition of the unit containing an amine function.

Compounds of this type may be represented by one of the following formulae:

$$HZ-(P')_n-ZH$$

or $$HZ-(P')_p-ZH$$

in which Z, P, P', n and p are as defined above.

Examples of compounds containing an amine function that may be mentioned include N-methyldiethanolamine, N-tert-butyldiethanolamine and N-sulfoethyldiethanolamine.

The second compound involved in the preparation of the polymer of formula (I) according to the invention is a diisocyanate corresponding to the formula:

$$O=C=N-R_4-N=C=O$$

in which $R_4$ is as defined above.

By way of example, mention may be made of methylenediphenyl diisocyanate, methylenecyclohexane diisocyanate, isophorone diisocyanate, toluene diisocyanate, naphthalene diisocyanate, butane diisocyanate and hexane diisocyanate.

A third compound involved in the preparation of the polymer of formula (I) according to the invention is a hydrophobic compound intended to form the terminal hydrophobic groups of the polymer of formula (I).

This compound consists of a hydrophobic group and of a function containing a labile hydrogen, for example a hydroxyl, primary or secondary amine, or thiol function.

By way of example, this compound may be a fatty alcohol such as, in particular, stearyl alcohol, dodecyl alcohol or decyl alcohol. When this compound comprises a polymeric chain, it may be, for example, [lacuna]-hydroxylated hydrogenated polybutadiene.

The hydrophobic group of the compound of formula (I) according to the invention may also result from the quaternization reaction of the tertiary amine of the compound comprising at least one tertiary amine unit. Thus, the hydrophobic group is introduced via the quaternizing agent. This quaternizing agent is a compound of the type RQ or R'Q, in which R and R' are as defined above and Q denotes a leaving group such as a halide, a sulfate, etc.

The cationic associative amphiphilic polymer of the invention may also comprise a hydrophilic block. This block is provided by a fourth type of compound involved in the preparation of the polymer. This compound may be multifunctional. It is preferably difunctional. It is also possible to have a mixture in which the percentage of multifunctional compound is low.

The functions containing a labile hydrogen are alcohol, primary or secondary amine or thiol functions. This compound may be a polymer terminated at the chain ends with one of these functions containing a labile hydrogen.

By way of example, when it is not a polymer, mention may be made of ethylene glycol, diethylene glycol and propylene glycol.

When it is a hydrophilic polymer, mention may be made, for example, of polyethers, sulfonated polyesters and sulfonated polyamides, or a mixture of these polymers. The hydrophilic compound is preferentially a polyether and especially a poly(ethylene oxide) or poly(propylene oxide).

The polymer prepared from the compounds defined above is a cationic associative amphiphilic polymer of formula (I) according to the present invention. This polymer is soluble or dispersible in water and produces a spectacular increase in the viscosity of the aqueous solution into which it is dissolved or dispersed.

The hydrophilic group termed Y in formula (I) is optional. Specifically, the units containing a quaternary amine or protonated function may suffice to provide the solubility or water-dispersibility required for this type of polymer in an aqueous solution.

Although the presence of a hydrophilic group Y is optional, cationic associative amphiphilic polyurethanes comprising such a group are, however, preferred.

The cationic polyurethanes according to the invention are preferably water-soluble or water-dispersible.

The terms "water-soluble" and "water-dispersible" regarding the associative polyurethanes of the present invention mean that these polymers have a solubility in water at room temperature at least equal to 1% by weight, i.e. up to this concentration, no precipitate may be detected by the naked eye and the solution is totally clear and homogeneous.

The expression "water-dispersible" polyurethanes means polymers which, when suspended in water, spontaneously form globules that have a mean size, measured by light scattering using a Coulter machine, of between 5 nm and 600 nm and in particular between 5 nm and 500 nm.

The cationic associative polyurethanes are preferably used in an amount that can range from about 0.01% to 10% by weight relative to the total weight of the composition for treating keratin materials. This amount more preferably ranges from about 0.1% to 5% by weight.

The protecting agents for keratin materials may be any active agent that is useful for preventing or limiting degradation caused by physical or chemical attack.

Thus, the protecting agent for keratin materials may be chosen from UV-screening agents, free-radical scavengers, antioxidants, vitamins, provitamins and sequestering agents.

The UV-screening agents (systems for screening out UV radiation) are chosen especially from water-soluble or liposoluble, silicone or nonsilicone screening agents and mineral oxide nanoparticles whose surface has optionally been treated to make them hydrophilic or hydrophobic.

The water-soluble UV-screening agents may be chosen, for example, from para-aminobenzoic acid and its salts, anthranilic acid and its salts, salicylic acid and its salts, p-hydroxycinnamic acid and its salts, sulfonic derivatives of benz-x-azoles (benzothiazoles, benzimidazoles and benzoxazoles) and salts thereof, sulfonic derivatives of benzophenone and salts thereof, sulfonic derivatives of benzylidenecamphor and salts thereof, benzylidenecamphor derivatives substituted with a quaternary amine and salts thereof, phthalylidenecamphorsulfonic acid derivatives and salts thereof, and sulfonic derivatives of benzotriazole.

It is also possible to use hydrophilic polymers having, in addition and on account of their chemical nature, UV-photoprotective properties. Mention may be made of polymers comprising benzylidenecamphor and/or benzotriazole groups, substituted with sulfonic or quaternary ammonium groups.

As liposoluble (or lipophilic) UV-screening agents that are suitable for use in the present invention, mention may be made especially of: p-aminobenzoic acid derivatives, such as p-aminobenzoic acid esters or amides; salicylic acid derivatives such as the esters; benzophenone derivatives; dibenzoylmethane derivatives; diphenylacrylate derivatives; benzofuran derivatives; polymeric UV-screening agents containing one or more organosilicon residues; cinnamic acid esters; camphor derivatives; trianilino-s-triazine derivatives; urocanic acid ethyl ester; benzotriazoles; hydroxyphenyltriazine derivatives; bis-resorcinol-dialkylaminotriazines; and mixtures thereof.

The liposoluble (or lipophilic) UV-screening agent according to the invention is preferably chosen from: octyl salicylate; 4-tert-butyl-4'-methoxydibenzoylmethane (Parsol 1789 from Givaudan); octocrylene; 2-ethylhexyl 4-methoxycinnamate (Parsol MCX) and the compound of formula (II) below, or 2-(2H-benzotriazol-2-yl)-4-methyl-6-[2-methyl-3-[1,3,3,3-tetramethyl-1-[(trimethylsilyl)oxy]disiloxanyl]-propynyl]phenol, described in patent application EP-A-0 392 883:

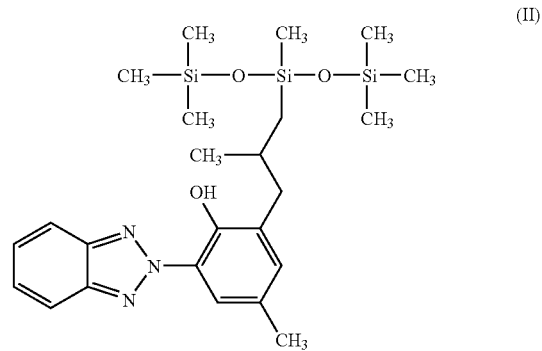

(II)

Other UV-screening agents that are particularly preferred according to the invention are benzophenone derivatives such as Uvinul MS 40 (2-hydroxy-4-methoxybenzophenone-5-sulfonic acid) and Uvinul M40 (2-hydroxy-4-methoxybenzophenone) sold by BASF, benzalmalonate derivatives such as Parsol SLX (polydimethyl/methyl (3-(4-(2,2-bis-ethoxy-carbonylvinyl)phenoxy)propenyl)siloxane) sold by Givaudan-Rouré, benzylidenecamphor derivatives such as Mexoryl SX (β,β'-camphorsulfonic [1,4-divinylbenzene]

acid) manufactured by the company Chimex, and benzimidazole derivatives such as Eusolex 232 (2-phenylbenzimidazole-5-sulfonic acid) sold by Merck.

The mineral oxides may be chosen from titanium oxides, zinc oxides and cerium oxides.

The antioxidants and/or free-radical scavengers are chosen especially from phenols such as BHA (tert-butyl-4-hydroxyanisole), BHT (2,6-di-tert-butyl-p-cresol), TBHQ (tert-butylhydroquinone), polyphenols such as proanthocyanidol oligomers and flavonoids, hindered amines known under the generic term HALS (Hindered Amine Light Stabilizer) such as tetraminopiperidine, erythorbic acid, polyamines such as spermine, cysteines, glutathione, superoxide dismutase and lactoferrin.

The vitamins are chosen especially from ascorbic acid, vitamin E, vitamin E acetate, B vitamins such as vitamins B3 and B5, vitamin PP, and vitamin A and its derivatives.

The provitamins are chosen especially from panthenol and retinol.

The sequestering agents are chosen especially from the Dequest products such as diethylenetriamine-pentamethylenephosphonic acid and diethylenetriamine-tetramethylenephosphonic acid and salts thereof, EDTA (ethylenediaminetetraacetic acid) and its salts, especially the sodium or potassium salts.

According to the invention, the protecting agent(s) for keratin materials may represent from 0.001% to 20% by weight, preferably from 0.01% to 10% by weight and more particularly from 0.1% to 5% by weight, relative to the total weight of the final composition.

In the context of the present patent application, the term "conditioner" means any agent whose function is to improve the cosmetic properties of the hair, in particular the softness, disentangling, feel and static electricity.

The conditioners may be in liquid, semi-solid or solid form such as, for example, oils, waxes or gums.

According to the invention, the conditioners may be chosen from synthetic oils such as polyolefins, mineral oils, plant oils, fluoro oils or perfluoro oils, natural or synthetic waxes, silicones, cationic polymers, compounds of ceramide type, cationic surfactants, fatty amines, fatty acids and derivatives thereof, fatty alcohols and derivatives thereof, and also mixtures of these various compounds.

The conditioners that are preferred according to the invention are cationic polymers and silicones.

The synthetic oils are especially polyolefins, in particular poly-α-olefins and more particularly:
of hydrogenated or nonhydrogenated polybutene type, and preferably hydrogenated or nonhydrogenated polyisobutene.

Isobutylene oligomers with a molecular weight of less than 1000 and mixtures thereof with polyisobutylenes with a molecular weight of greater than 1000, and preferably between 1000 and 15 000, are preferably used.

As examples of poly-α-olefins that can be used in the context of the present invention, mention may be made more particularly of the products sold under the name Permethyl 99 A, 101 A, 102 A, 104 A (n=16) and 106 A (n=38) by the company Presperse Inc., or alternatively the products sold under the name Arlamol HD (n=3) by the company ICI (n denoting the degree of polymerization),
of hydrogenated or nonhydrogenated polydecene type.

Such products are sold, for example, under the names Ethylflo by the company Ethyl Corp. and Arlamol PAO by the company ICI.

The mineral oils that may be used in the compositions of the invention are preferably chosen from the group formed by:
hydrocarbons, such as hexadecane and liquid paraffin.

The animal or plant oils are preferably chosen from the group formed by sunflower oil, corn oil, soybean oil, avocado oil, jojoba oil, marrow oil, grapeseed oil, sesame oil, hazelnut oil, fish oils, glyceryl tricaprocaprylate, or plant or animal oils of formula $R_9COOR_{10}$ in which $R_9$ represents a higher fatty acid residue containing from 7 to 29 carbon atoms and $R_{10}$ represents a linear or branched hydrocarbon-based chain containing from 3 to 30 carbon atoms, in particular alkyl or alkenyl, for example purcellin oil or liquid jojoba wax.

It is also possible to use natural or synthetic essential oils such as, for example, eucalyptus oil, lavendin oil, lavender oil, vetiver oil, *Litsea cubeba* oil, lemon oil, sandalwood oil, rosemary oil, camomile oil, savory oil, nutmeg oil, cinnamon oil, hyssop oil, caraway oil, orange oil, geraniol oil, cade oil and bergamot oil.

The waxes are natural (animal or plant) or synthetic substances that are solid at room temperature (20°-25° C.). They are insoluble in water, soluble in oils and are capable of forming a water-repellent film.

For the definition of waxes, mention may be made, for example, of P. D. Dorgan, Drug and Cosmetic Industry, December 1983, pp. 30-33.

The wax(es) is(are) chosen in particular from carnauba wax, candelilla wax, alfalfa wax, paraffin wax, ozokerite, plant waxes such as olive tree wax, rice wax, hydrogenated jojoba wax or the absolute waxes of flowers such as the essential wax of blackcurrant flower sold by the company Bertin (France), animal waxes such as beeswaxes, or modified beeswaxes (cerabellina); other waxes or waxy starting materials which can be used according to the invention are, in particular, marine waxes such as the product sold by the company Sophim under the reference M82, and polyethylene waxes or polyolefins in general.

The conditioners of cationic polymer type that may be used in accordance with the present invention may be chosen from all those already known per se as improving the cosmetic properties of hair treated with detergent compositions, i.e. especially those described in patent application EP-A-337 354 and in French patents FR-A-2 270 846, 2 383 660, 2 598 611, 2 470 596 and 2 519 863.

Even more generally, for the purpose of the present invention, the term "cationic polymer" denotes any polymer containing cationic groups and/or groups that may be ionized into cationic groups.

The cationic polymers that are preferred are chosen from those containing units comprising primary, secondary, tertiary and/or quaternary amine groups that may either form part of the main polymer chain or may be borne by a side substituent directly attached thereto.

The cationic polymers used generally have a number-average molecular mass of between 500 and $5 \times 10^6$ approximately and preferably between $10^3$ and $3 \times 10^6$ approximately.

Among the cationic polymers that may be mentioned more particularly are polymers of the polyamine, polyamino amide and polyquaternary ammonium type. These are known products.

The polymers of the polyamine, polyamino amide and polyquaternary ammonium type that may be used in accordance with the present invention, and that may especially be mentioned, are those described in French patents Nos 2 505 348 and 2 542 997. Among these polymers, mention may be made of:

(1) homopolymers or copolymers derived from acrylic or methacrylic esters or amides and comprising at least one of the units of the following formulae:

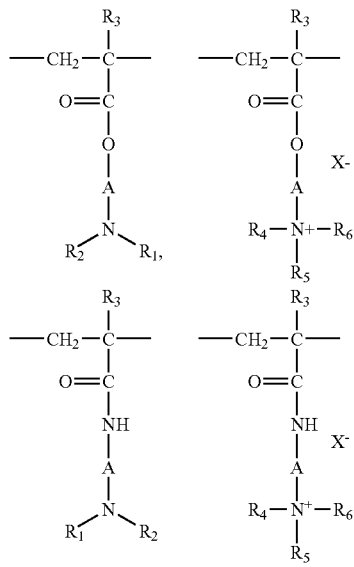

in which:
R$_3$, which may be identical or different, denote a hydrogen atom or a CH$_3$ radical;
A, which may be identical or different, represent a linear or branched alkyl group of 1 to 6 carbon atoms, preferably 2 or 3 carbon atoms, or a hydroxyalkyl group of 1 to 4 carbon atoms;
R$_4$, R$_5$ and R$_6$, which may be identical or different, represent an alkyl group containing from 1 to 18 carbon atoms or a benzyl radical and preferably an alkyl group containing from 1 to 6 carbon atoms;
R$_1$ and R$_2$, which may be identical or different, represent hydrogen or an alkyl group containing from 1 to 6 carbon atoms, and preferably methyl or ethyl;
X denotes an anion derived from a mineral or organic acid, such as a methosulfate anion or a halide such as chloride or bromide.

The polymers of family (1) can also contain one or more units derived from comonomers which may be chosen from the family of acrylamides, methacrylamides, diacetone acrylamides, acrylamides and methacrylamides substituted on the nitrogen with lower (C$_1$-C$_4$) alkyls, acrylic or methacrylic acids or esters thereof, vinyllactams such as vinylpyrrolidone or vinylcaprolactam, and vinyl esters.

Thus, among these polymers of family (1), mention may be made of:
copolymers of acrylamide and of dimethylaminoethyl methacrylate quaternized with dimethyl sulfate or with a dimethyl halide, such as the product sold under the name Hercofloc by the company Hercules,
the copolymers of acrylamide and of methacryloyloxyethyltrimethylammonium chloride described, for example, in patent application EP-A-080 976 and sold under the name Bina Quat P 100 by the company Ciba Geigy,
the copolymer of acrylamide and of methacryloyloxy-ethyltrimethylammonium methosulfate sold under the name Reten by the company Hercules,
quaternized or nonquaternized vinylpyrrolidone/dialkylaminoalkyl acrylate or methacrylate copolymers, such as the products sold under the name Gafquat by the company ISP, such as, for example, Gafquat 734 or Gafquat 755, or alternatively the products known as Copolymer 845, 958 and 937. These polymers are described in detail in French patents 2 077 143 and 2 393 573,
dimethylaminoethyl methacrylate/vinylcaprolactam/vinylpyrrolidone terpolymers, such as the product sold under the name Gaffix VC 713 by the company ISP,
vinylpyrrolidone/methacrylamidopropyldimethylamine copolymers sold in particular under the name Styleze CC 10 by ISP, and
quaternized vinylpyrrolidone/dimethylaminopropylmethacrylamide copolymers, such as the product sold under the name Gafquat HS 100 by the company ISP.
(2) The cellulose ether derivatives containing quaternary ammonium groups, described in French patent 1 492 597, and in particular polymers sold under the name "JR" (JR 400, JR 125 and JR 30M) or "LR" (LR 400 or LR 30M) by the company Union Carbide Corporation. These polymers are also defined in the CTFA dictionary as quaternary ammoniums of hydroxyethylcellulose that have reacted with an epoxide substituted with a trimethylammonium group.
(3) Cationic cellulose derivatives such as cellulose copolymers or cellulose derivatives grafted with a water-soluble quaternary ammonium monomer, and described in particular in U.S. Pat. No. 4,131,576, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.

The commercial products corresponding to this definition are more particularly the products sold under the names Celquat L 200 and Celquat H 100 by the company National Starch.
(4) The cationic polysaccharides described more particularly in U.S. Pat. Nos. 3,589,578 and 4,031,307, such as guar gums containing cationic trialkylammonium groups. Guar gums modified with a salt (e.g. chloride) of 2,3-epoxypropyltrimethylammonium are used, for example.

Such products are sold in particular under the trade names Jaguar C13 S, Jaguar C 15, Jaguar C 17 and Jaguar C162 by the company Meyhall.
(5) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, as well as the oxidation and/or quaternization products of these polymers. Such polymers are described, in particular, in French patents 2 162 025 and 2 280 361.
(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508.
(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylene-triamine polymers in which the alkyl radical contains from 1 to 4 carbon atoms and preferably denotes methyl, ethyl or propyl. Such polymers are described in particular in French patent 1 583 363.

Among these derivatives, mention may be made more particularly of the adipic acid/dimethylaminohydroxypropyl/diethylenetriamine polymers sold under the name Cartaretine F, F4 or F8 by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name Hercosett 57 by the company Hercules Inc. or alternatively under the name PD 170 or Delsette 101 by the company Hercules in the case of the adipic acid/epoxypropyl/diethylenetriamine copolymer.

(9) Cyclopolymers of alkyldiallylamine or of dialkyldiallylammonium, such as the homopolymers or copolymers containing, as main constituent of the chain, units corresponding to formula (VI) or (VI'):

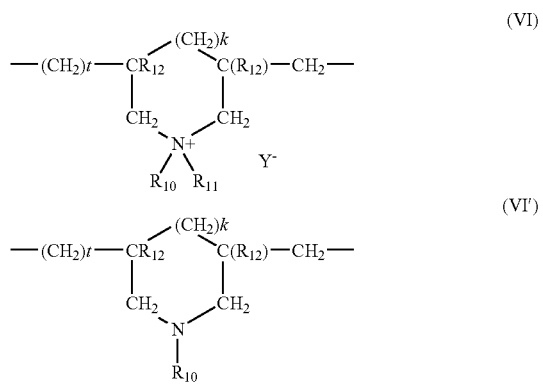

in which formulae k and t are equal to 0 or 1, the sum k+t being equal to 1; $R_{12}$ denotes a hydrogen atom or a methyl radical; $R_{10}$ and $R_{11}$, independently of each other, denote an alkyl group having from 1 to 22 carbon atoms, a hydroxyalkyl group in which the alkyl group preferably has 1 to 5 carbon atoms, a lower ($C_1$-$C_4$) amidoalkyl group, or $R_{10}$ and $R_{11}$ can denote, together with the nitrogen atom to which they are attached, heterocyclic groups such as piperidyl or morpholinyl; $Y^-$ is an anion such as bromide, chloride, acetate, borate, citrate, tartrate, bisulfate, bisulfite, sulfate or phosphate. These polymers are described in particular in French patent 2 080 759 and in its Certificate of Addition 2 190 406.

$R_{10}$ and $R_{11}$, independently of each other, preferably denote an alkyl group containing from 1 to 4 carbon atoms.

Among the polymers defined above, mention may be made more particularly of the dimethyldiallylammonium chloride homopolymer sold under the name Merquat 100 by the company Calgon (and its homologs of low weight-average molecular mass) and the copolymers of diallyldimethylammonium chloride and of acrylamide, sold under the name Merquat 550.

(10) The quaternary diammonium polymer containing repeating units corresponding to the formula:

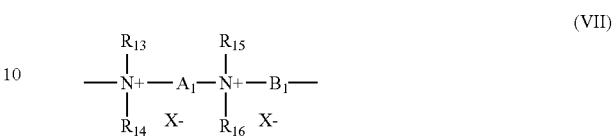

in which formula (VII):
$R_{13}$, $R_{14}$, $R_{15}$ and $R_{16}$, which may be identical or different, represent aliphatic, alicyclic or arylaliphatic radicals containing from 1 to 20 carbon atoms or lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally containing a second hetero atom other than nitrogen, or alternatively $R_{13}$, $R_{14}$, $R_{15}$ and $R_{16}$ represent a linear or branched $C_1$-$C_6$ alkyl radical substituted with a nitrile, ester, acyl or amide group or a group —CO—O—$R_{17}$-D or —CO—NH—$R_{17}$-D where $R_{17}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid;
$A_1$, $R_{13}$ and $R_{15}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group —$(CH_2)_n$—CO-D-OC—$(CH_2)_n$— in which D denotes:

a) a glycol residue of formula: —O—Z—O—, where Z denotes a linear or branched hydrocarbon-based radical or a group corresponding to one of the following formulae:

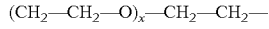

$(CH_2$—$CH_2$—$O)_x$—$CH_2$—$CH_2$—

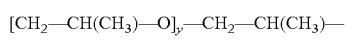

$[CH_2$—$CH(CH_3)$—$O]_y$—$CH_2$—$CH(CH_3)$— where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon-based radical, or alternatively the divalent radical

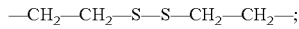

—$CH_2$—$CH_2$—S—S—$CH_2$—$CH_2$—;

d) a ureylene group of formula: —NH—CO—NH—.
Preferably, $X^-$ is an anion such as chloride or bromide.
These polymers generally have a number-average molecular mass of between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to the formula:

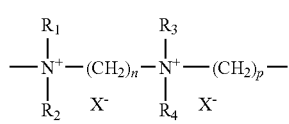
(a)

in which $R_1$, $R_2$, $R_3$ and $R_4$, which may be identical or different, denote an alkyl or hydroxyalkyl radical containing from 1 to 4 carbon atoms approximately, n and p are integers ranging from 2 to 20 approximately, and $X^-$ is an anion derived from a mineral or organic acid.

A compound of formula (a) that is particularly preferred is the compound for which $R_1$, $R_2$, $R_3$ and $R_4$ represent a methyl radical and n=3, p=6 and X-Cl, referred to as hexadimethrine chloride according to the INCI nomenclature (CTFA).

(11) polyquaternary ammonium polymers consisting of units of formula (VIII):

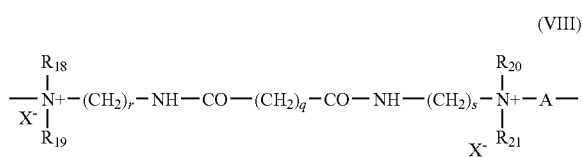
(VIII)

in which formula:

$R_{18}$, $R_{19}$, $R_{20}$ and $R_{21}$, which may be identical or different, represent a hydrogen atom or a methyl, ethyl, propyl, β-hydroxyethyl, β-hydroxypropyl or —$CH_2CH_2(OCH_2CH_2)_p$OH radical, where p is equal to 0 or to an integer between 1 and 6, with the proviso that $R_{18}$, $R_{19}$, $R_{20}$ and $R_{21}$ do not simultaneously represent a hydrogen atom, r and s, which may be identical or different, are integers ranging from 1 to 6, q is equal to 0 or to an integer ranging from 1 to 34, $X^-$ denotes an anion such as a halide, A denotes a divalent radical or preferably represents —$CH_2$—$CH_2$—O—$CH_2$—$CH_2$—.

Such compounds are described in particular in patent application EP-A-122 324.

Among these products, mention may be made, for example, of Mirapol® A 15, Mirapol® AD1, Mirapol® AZ1 and Mirapol® 175 sold by the company Miranol.

(12) Quaternary polymers of vinylpyrrolidone and of vinylimidazole, such as, for example, the products sold under the names Luviquat® FC 905, FC 550 and FC 370 by the company BASF.

(13) Polyamines such as Polyquart® H sold by Henkel, which is given under the reference name "Polyethylene glycol (15) tallow polyamine" in the CTFA dictionary.

(14) Crosslinked methacryloyloxy($C_1$-$C_4$)alkyltri-($C_1$-$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethylammonium chloride copolymer (20/80 by weight) in the form of a dispersion containing 50% by weight of said copolymer in mineral oil can be used more particularly. This dispersion is sold under the name Salcare® SC 92 by the company Allied Colloids. A crosslinked methacryloyloxyethyltrimethylammonium chloride homopolymer containing about 50% by weight of the homopolymer in mineral oil or in a liquid ester can also be used. These dispersions are sold under the names Salcare® SC 95 and Salcare® SC 96 by the company Allied Colloids.

Other cationic polymers that can be used in the context of the invention are cationic proteins or cationic protein hydrolyzates, polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers that may be used in the context of the present invention, it is preferred to use quaternary cellulose ether derivatives such as the products sold under the name JR 400 by the company Union Carbide Corporation, cationic cyclopolymers, in particular the dimethyldiallylammonium chloride homopolymers or copolymers sold under the names Merquat 100, Merquat 550 and Merquat S by the company Calgon, and quaternary polymers of vinylpyrrolidone and of vinylimidazole, and mixtures thereof.

The silicones that may be used in accordance with the invention are in particular polyorganosiloxanes that are insoluble in the composition and that may be in the form of oils, waxes, resins or gums.

The organopolysiloxanes are defined in greater detail in Walter Noll's "Chemistry and Technology of Silicones" (1968) Academic Press. They can be volatile or nonvolatile.

When they are volatile, the silicones are more particularly chosen from those having a boiling point of between 60° C. and 260° C., and even more particularly from:

(i) cyclic silicones containing from 3 to 7 and preferably 4 to 5 silicon atoms. These are, for example, octamethylcyclotetrasiloxane sold in particular under the name Volatile Silicone 7207 by Union Carbide or Silbione 70045 V 2 by Rhône-Poulenc, decamethylcyclopentasiloxane sold under the name Volatile Silicone 7158 by Union Carbide, and Silbione 70045 V 5 by Rhône-Poulenc, and mixtures thereof.

Mention may also be made of cyclocopolymers of the dimethylsiloxanes/methylalkylsiloxane type, such as Volatile Silicone FZ 3109 sold by the company Union Carbide, having the chemical structure:

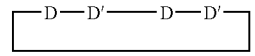

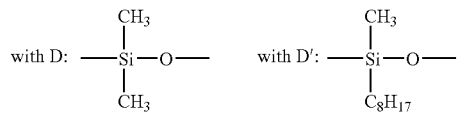

Mention may also be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones containing 2 to 9 silicon atoms and having a viscosity of less than or equal to $5\times10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers "Volatile Silicone Fluids for Cosmetics".

Nonvolatile silicones, and more particularly polyalkylsiloxanes, polyarylsiloxanes, polyalkylarylsiloxanes, silicone gums and resins, polyorganosiloxanes modified with organofunctional groups, and mixtures thereof, are preferably used.

These silicones are more particularly chosen from polyalkylsiloxanes, among which mention may be made mainly of polydimethylsiloxanes containing trimethylsilyl end groups having a viscosity of from $5\times10^{-6}$ to 2.5 m$^2$/s at 25° C. and preferably $1\times10^{-5}$ to 1 m$^2$/s. The viscosity of the silicones is measured, for example, at 25° C. according to ASTM standard 445 Appendix C.

Among these polyalkylsiloxanes, mention may be made, in a nonlimiting manner, of the following commercial products:

the Silbione oils of the 47 and 70 047 series or the Mirasil oils sold by Rhône-Poulenc, such as, for example, the oil 70 047 V 500 000;

the oils of the Mirasil series sold by the company Rhône-Poulenc;

the oils of the 200 series from the company Dow Corning, such as, more particularly, DC200 with a viscosity of 60 000 cSt;

the Viscasil oils from General Electric and certain oils of the SF series (SF 96, SF 18) from General Electric.

Mention may also be made of polydimethylsiloxanes containing dimethylsilanol end groups (Dimethiconol according to the CTFA name) such as the oils of the 48 series from the company Rhône-Poulenc.

In this category of polyalkylsiloxanes, mention may also be made of the products sold under the names Abil Wax 9800 and 9801 by the company Goldschmidt, which are poly($C_1$-$C_{20}$)alkylsiloxanes.

The polyalkylarylsiloxanes are chosen particularly from linear and/or branched polydimethylmethylphenylsiloxanes and polydimethyldiphenylsiloxanes with a viscosity of from $1\times10^{-5}$ to $5\times10^{-2}$ m$^2$/s at 25° C.

Among these polyalkylarylsiloxanes, mention may be made, by way of example, of the products sold under the following names:

the Silbione oils of the 70 641 series from Rhône-Poulenc;
the oils of the Rhodorsil 70 633 and 763 series from Rhône-Poulenc;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

The silicone gums that can be used in accordance with the invention are, in particular, polydiorganosiloxanes having high number-average molecular masses of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecanes, or mixtures thereof.

Mention may be made more particularly of the following products:
polydimethylsiloxane,
polydimethylsiloxane/methylvinylsiloxane gums,
polydimethylsiloxane/diphenylsiloxiane,
polydimethylsiloxane/phenylmethylsiloxane,
polydimethylsiloxane/diphenylsiloxane/methylvinylsiloxane.

Products that can be used more particularly in accordance with the invention are mixtures such as:

mixtures formed from a polydimethylsiloxane hydroxylated at the chain end (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;

mixtures of two PDMSs of different viscosities, and more particularly of a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5\times10^{-6}$ m$^2$/s. This product preferably contains 15% SE 30 gum and 85% SF 96 oil.

The organopolysiloxane resins that can be used in accordance with the invention are crosslinked siloxane systems containing the following units: $R_2SiO_{2/2}$, $R_3SiO_{1/2}$, $RSiO_{3/2}$ and $SiO_{4/2}$ in which R represents a hydrocarbon-based group containing 1 to 16 carbon atoms or a phenyl group. Among these products, those particularly preferred are the ones in which R denotes a $C_1$-$C_4$ lower alkyl radical, more particularly methyl, or a phenyl radical.

Among these resins, mention may be made of the product sold under the name Dow Corning 593 or those sold under the names Silicone Fluid SS 4230 and SS 4267 by the company General Electric, which are silicones of dimethyl/trimethyl siloxane structure.

Mention may also be made of the trimethyl siloxysilicate type resins sold in particular under the names X22-4914, X21-5034 and X21-5037 by the company Shin-Etsu.

The organomodified silicones that can be used in accordance with the invention are silicones as defined above and containing in their structure one or more organofunctional groups attached via a hydrocarbon-based radical.

Among the organomodified silicones, mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet L 722, L 7500, L 77 and L 711 by the company Union Carbide, and the ($C_{12}$)alkylmethicone copolyol sold by the company Dow Corning under the name Q2 5200;

substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, in particular, $C_1$-$C_4$ aminoalkyl groups;

thiol groups such as the products sold under the names GP 72 A and GP 71 from Genesee;

alkoxylated groups such as the product sold under the name Silicone Copolymer F-755 by SWS Silicones and Abil Wax 2428, 2434 and 2440 by the company Goldschmidt;

hydroxylated groups such as the polyorganosiloxanes containing a hydroxyalkyl function, described in French patent application FR-A-85/16334, corresponding to formula (IX):

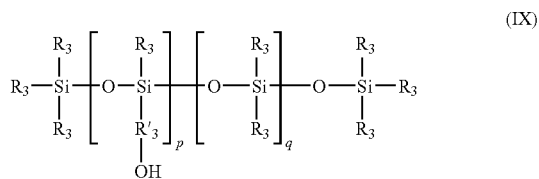

(IX)

in which the radicals $R_3$, which may be identical or different, are chosen from methyl and phenyl radicals; at least 60 mol % of the radicals $R_3$ denoting methyl; the radical $R'_3$ is a $C_2$-$C_{18}$ divalent hydrocarbon-based alkylene chain unit; p is between 1 and 30 inclusive; q is between 1 and 150 inclusive;

acyloxyalkyl groups such as, for example, the polyorganosiloxanes described in U.S. Pat. No. 4,957,732 and corresponding to formula (X):

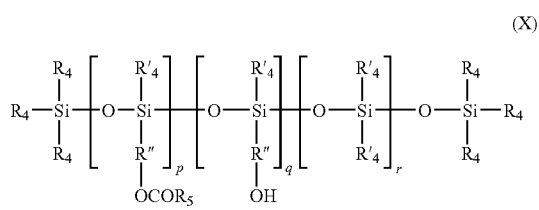

(X)

in which:
$R_4$ denotes a methyl, phenyl, —$OCR_5$ or hydroxyl group, one of the radicals $R_4$ per silicon atom possibly being OH;
$R'_4$ denotes methyl or phenyl; at least 60 mol % of all the radicals $R_4$ and $R'_4$ denoting methyl;
$R_5$ denotes $C_8$-$C_{20}$ alkyl or alkenyl;
R" denotes a $C_2$-$C_{18}$ linear or branched divalent hydrocarbon-based alkylene radical;
r is between 1 and 120 inclusive;
p is between 1 and 30;
q is equal to 0 or is less than 0.5 p, p+q being between 1 and 30; the polyorganosiloxanes of formula (VI) may contain groups:

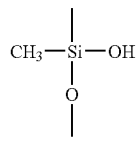

in proportions not exceeding 15% of the sum p+q+r.

anionic groups of carboxylic type, such as, for example, in the products described in patent EP 186 507 from the company Chisso Corporation, or of alkylcarboxylic type, such as those present in the product X-22-3701E from the company Shin-Etsu; 2-hydroxyalkyl sulfonate; 2-hydroxyalkyl thiosulfate such as the products sold by the company Goldschmidt under the names Abil S201 and Abil S255;

hydroxyacylamino groups, such as the polyorganosiloxanes described in patent application EP 342 834. Mention may be made, for example, of the product Q2-8413 from the company Dow Corning.

According to the invention, it is also possible to use silicones comprising a polysiloxane portion and a portion consisting of a nonsilicone organic chain, one of the two portions constituting the main chain of the polymer, the other being grafted onto said main chain. These polymers are described, for example, in patent applications EP-A-412 704, EP-A-412 707, EP-A-640 105, WO 95/00578, EP-A-582 152 and WO 93/23009 and U.S. Pat. Nos. 4,693,935, 4,728,571 and 4,972, 037. These polymers are preferably anionic or nonionic.

Such polymers are, for example, copolymers that can be obtained by free-radical polymerization starting with a monomer mixture consisting of:
a) 50 to 90% by weight of tert-butyl acrylate;
b) 0 to 40% by weight of acrylic acid;
c) 5 to 40% by weight of silicone macromer of formula:

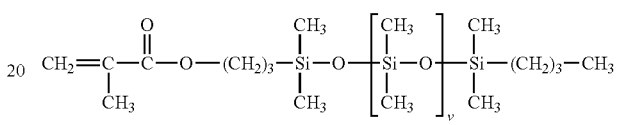

with v being a number ranging from 5 to 700; the weight percentages being calculated relative to the total weight of the monomers.

Other examples of grafted silicone polymers are, in particular, polydimethylsiloxanes (PDMS) onto which are grafted, via a connecting chain unit of thiopropylene type, mixed polymer units of poly(meth)acrylic acid type and of polyalkyl (meth)acrylate type and polydimethylsiloxanes (PDMS) onto which are grafted, via a connecting chain unit of thiopropylene type, polymer units of polyisobutyl (meth) acrylate type.

According to the invention, all of the silicones can also be used in the form of emulsions, nanoemulsions or microemulsions.

The polyorganosiloxanes that are particularly preferred in accordance with the invention are:
nonvolatile silicones chosen from the family of polyalkylsiloxanes containing trimethylsilyl end groups, such as oils having a viscosity of between 0.2 and 2.5 $m^2$/s at 25° C., such as the oils of the DC200 series from Dow Corning, in particular that with a viscosity of 60 000 cSt, of the Silbione 70047 and 47 series and more particularly the oil 70 047 V 500 000, which are sold by the company Rhone-Poulenc, polyalkylsiloxanes containing dimethylsilanol end groups, such as dimethiconols, or polyalkylarylsiloxanes such as the oil Silbione 70641 V 200 sold by the company Rhône-Poulenc;
the organopolysiloxane resin sold under the name Dow Corning 593;
polysiloxanes containing amine groups, such as amodimethicones or trimethylsilylamodimethicones.

The cationic proteins or protein hydrolyzates are, in particular, chemically modified polypeptides bearing quaternary ammonium groups at the end of the chain or grafted thereto. Their molecular mass can range, for example, from 1500 to 10 000 and in particular from 2000 to 5000 approximately. Among these compounds, mention may be made in particular of:
collagen hydrolyzates bearing triethylammonium groups, such as the products sold under the name Quat-Pro E by the company Maybrook and referred to in the CTFA dictionary as "Triethonium Hydrolyzed Collagen Ethosulfate";
collagen hydrolyzates bearing trimethylammonium and trimethylstearylammonium chloride groups, sold under the name Quat-Pro S by the company Maybrook and referred to in the CTFA dictionary as "Steartrimonium Hydrolyzed Collagen";

animal protein hydrolyzates bearing trimethylbenzylammonium groups such as the products sold under the name Crotein BTA by the company Croda and referred to in the CTFA dictionary as "Benzyltrimonium hydrolyzed animal protein";

protein hydrolyzates bearing, on the polypeptide chain, quaternary ammonium groups containing at least one alkyl radical having from 1 to 18 carbon atoms.

Among these protein hydrolyzates, mention may be made, inter alia, of:

Croquat L in which the quaternary ammonium groups contain a $C_{12}$ alkyl group;

Croquat M in which the quaternary ammonium groups contain $C_{10}$-$C_{18}$ alkyl groups;

Croquat S in which the quaternary ammonium groups contain a $C_{18}$ alkyl group;

Crotein Q in which the quaternary ammonium groups contain at least one alkyl group having from 1 to 18 carbon atoms.

These various products are sold by the company Croda.

Other quaternized proteins or hydrolyzates are, for example, those corresponding to the formula:

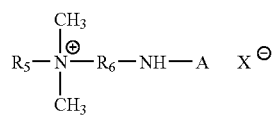

(XI)

in which $X^-$ is an anion of an organic or mineral acid, A denotes a protein residue derived from hydrolyzates of a protein, especially of collagen, $R_5$ denotes a lipophilic group containing up to 30 carbon atoms and $R_6$ represents an alkylene group having 1 to 6 carbon atoms. Mention may be made, for example, of the products sold by the company Inolex under the name Lexein QX 3000, referred to in the CTFA dictionary as "Cocotrimonium Collagen Hydrolysate".

Mention may also be made of quaternized plant proteins such as wheat, corn or soybean proteins: as quaternized wheat proteins, mention may be made of those sold by the company Croda under the names Hydrotriticum WQ or QM, referred to in the CTFA dictionary as "Cocodimonium Hydrolysed Wheat Protein", Hydrotriticum QL, referred to in the CTFA dictionary as "Lauridimonium Hydrolysed Wheat Protein" or Hydrotriticum QS, referred to in the CTFA dictionary as "Steardimonium Hydrolysed Wheat Protein".

According to the present invention, the compounds of ceramide type are in particular natural or synthetic ceramides and/or glycoceramides and/or pseudoceramides and/or neoceramides.

Compounds of ceramide type are described, for example, in patent applications DE 4 424 530, DE 4 424 533, DE 4 402 929, DE 4 420 736, WO 95/23807, WO 94/07844, EP-A-0 646 572, WO 95/16665, FR-2 673 179, EP-A-0 227 994, WO 94/07844, WO 94/24097 and WO 94/10131, the teachings of which are included herein by way of reference.

Compounds of ceramide type that are particularly preferred according to the invention are, for example:
2-N-linoleoylaminooctadecane-1,3-diol,
2-N-oleoylaminooctadecane-1,3-diol,
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol and in particular N-stearoylphytosphingosine,
2-N-palmitoylaminohexadecane-1,3-diol,
bis(N-hydroxyethyl-N-cetyl)malonamide,
N-(2-hydroxyethyl)-N-(3-cetyloxy-2-hydroxypropyl)cetylamide,
N-docosanoyl-N-methyl-D-glucamine,
or mixtures of these compounds.

It is also possible to use cationic surfactants, among which mention may be made in particular of: optionally polyoxyalkylenated primary, secondary or tertiary fatty amine salts; quaternary ammonium salts; imidazoline derivatives; or amine oxides of cationic nature.

Examples of quaternary ammonium salts include:

those of general formula (IV) below:

(IV)

in which the radicals $R_1$ to $R_4$, which may be identical or different, represent a linear or branched aliphatic radical containing from 1 to 30 carbon atoms, or an aromatic radical such as aryl or alkylaryl. The aliphatic radicals can comprise hetero atoms such as, in particular, oxygen, nitrogen, sulfur or halogens. The aliphatic radicals are chosen, for example, from alkyl, alkoxy, polyoxy($C_2$-$C_6$)alkylene, alkylamide, ($C_{12}$-$C_{22}$)alkylamido($C_2$-$C_6$)alkyl, ($C_{12}$-$C_{22}$)alkylacetate and hydroxyalkyl radicals, comprising from about 1 to 30 carbon atoms; $X^-$ is an anion chosen from the group of halides, phosphates, acetates, lactates, ($C_2$-$C_6$)alkyl sulfates and alkyl or alkylaryl sulfonates;

quaternary ammonium salts of imidazolinium, such as, for example, the salt of formula (V) below:

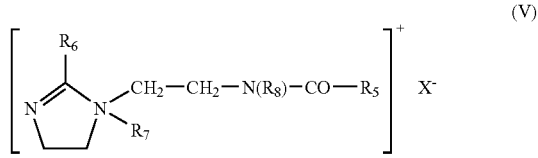

(V)

in which $R_5$ represents an alkenyl or alkyl radical containing from 8 to 30 carbon atoms, for example tallow fatty acid derivatives, $R_6$ represents a hydrogen atom, a $C_1$-$C_4$ alkyl radical or an alkenyl or alkyl radical containing from 8 to 30 carbon atoms, $R_7$ represents a $C_1$-$C_4$ alkyl radical, $R_8$ represents a hydrogen atom or a $C_1$-$C_4$ alkyl radical, $X^-$ is an anion chosen from the group of halides, phosphates, acetates, lactates, alkyl sulfates and alkyl or alkylaryl sulfonates. $R_5$ and $R_6$ preferably denote a mixture of alkenyl or alkyl radicals containing from 12 to 21 carbon atoms, for example tallow fatty acid derivatives, $R_7$ denotes a methyl radical and $R_8$ denotes a hydrogen atom. Such a product is sold, for example, under the name Rewoquat W 75 by the company Rewo;

diquaternary ammonium salts of formula (VI):

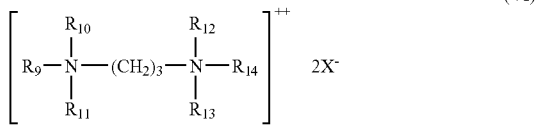

in which $R_9$ denotes an aliphatic radical containing from about 16 to 30 carbon atoms, $R_{10}$, $R_{11}$, $R_{12}$, $R_{13}$ and $R_{14}$, which may be identical or different, are chosen from hydrogen or an alkyl radical containing from 1 to 4 carbon atoms, and $X^-$ is an anion chosen from the group of halides, acetates, phosphates, nitrates and methyl sulfates. Such diquaternary ammonium salts in particular comprise propane tallow diammonium dichloride;

quaternary ammonium salts containing at least one ester function.

The quaternary ammonium salts containing at least one ester function that may be used according to the invention are, for example, those of formula (VII) below:

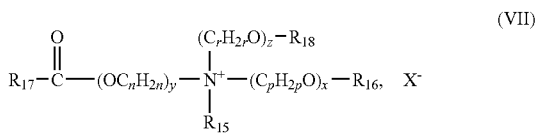

in which:

$R_{15}$ is chosen from $C_1$-$C_6$ alkyl radicals and $C_1$-$C_6$ hydroxyalkyl or dihydroxyalkyl radicals;

$R_{16}$ is chosen from:
a radical

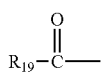

linear or branched, saturated or unsaturated $C_1$-$C_{22}$ hydrocarbon-based radicals $R_{20}$,
a hydrogen atom,
$R_{18}$ is chosen from:
a radical

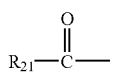

linear or branched, saturated or unsaturated $C_1$-$C_6$ hydrocarbon-based radicals $R_{22}$,
a hydrogen atom,
$R_{17}$, $R_{19}$ and $R_{21}$, which may be identical or different, are chosen from linear or branched, saturated or unsaturated $C_7$-$C_{21}$ hydrocarbon-based radicals;
n, p and r, which may be identical or different, are integers ranging from 2 to 6;
y is an integer ranging from 1 to 10;
x and z, which may be identical or different, are integers ranging from 0 to 10;

$X^-$ is a simple or complex, organic or inorganic anion;
with the proviso that the sum x+y+z is from 1 to 15, that when x is 0, then $R_{16}$ denotes $R_{20}$ and that when z is 0, then $R_{18}$ denotes $R_{22}$.

The $R_{15}$ alkyl radicals may be linear or branched and more particularly linear.

$R_{15}$ preferably denotes a methyl, ethyl, hydroxyethyl or dihydroxypropyl radical and more particularly a methyl or ethyl radical.

The sum x+y+z is advantageously from 1 to 10.

When $R_{16}$ is a hydrocarbon-based radical $R_{20}$, it may be long and contain from 12 to 22 carbon atoms, or short and contain from 1 to 3 carbon atoms.

When $R_{18}$ is a hydrocarbon-based radical $R_{22}$, it preferably contains 1 to 3 carbon atoms.

$R_{17}$, $R_{19}$ and $R_{21}$, which may be identical or different, are advantageously chosen from linear or branched, saturated or unsaturated $C_{11}$-$C_{21}$ hydrocarbon-based radicals, and more particularly from linear or branched, saturated or unsaturated, $C_{11}$-$C_{21}$ alkyl and alkenyl radicals.

x and z, which may be identical or different, are preferably 0 or 1.

y is advantageously equal to 1.

n, p and r, which may be identical or different, are preferably 2 or 3 and even more particularly are equal to 2.

The anion is preferably a halide (chloride, bromide or iodide) or an alkyl sulfate, more particularly methyl sulfate. However, methanesulfonate, phosphate, nitrate, tosylate, an anion derived from an organic acid, such as acetate or lactate, or any other anion that is compatible with the ammonium containing an ester function, may be used.

The anion $X^-$ is even more particularly chloride or methyl sulfate.

The ammonium salts more particularly used in the composition according to the invention are those of formula (VII) in which:

$R_{15}$ denotes a methyl or ethyl radical,
x and y are equal to 1;
z is equal to 0 or 1;
n, p and r are equal to 2;
$R_{16}$ is chosen from:
a radical

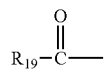

methyl, ethyl or $C_{14}$-$C_{22}$ hydrocarbon-based radicals;
a hydrogen atom;
$R_{18}$ is chosen from:
a radical

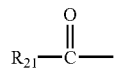

a hydrogen atom;
$R_{17}$, $R_{19}$ and $R_{21}$, which may be identical or different, are chosen from linear or branched, saturated or unsaturated $C_{13}$-$C_{17}$ hydrocarbon-based radicals and preferably from linear or branched, saturated or unsaturated $C_{13}$-$C_{17}$ alkyl and alkenyl radicals.

The hydrocarbon-based radicals are advantageously linear.

Examples that may be mentioned include the compounds of formula (VII) such as the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl radicals preferably contain 14 to 18 carbon atoms and are obtained more particularly from a plant oil such as palm oil or sunflower oil. When the compound contains several acyl radicals, these radicals may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization using an alkylating agent such as an alkyl halide (preferably a methyl or ethyl halide), a dialkyl sulfate (preferably dimethyl or diethyl sulfate), methyl methanesulfonate, methyl para-toluenesulfonate, glycol chlorohydrin or glycerol chlorohydrin.

Such compounds are sold, for example, under the names Dehyquart by the company Henkel, Stepanquat by the company Stepan, Noxamium by the company CECA or Rewoquat WE 18 by the company Rewo-Witco.

It is also possible to use the ammonium salts containing at least one ester function that are described in U.S. Pat. No. 4,874,554 and U.S. Pat. No. 4,137,180.

Among the quaternary ammonium salts of formula (IV), the ones that are preferred are, on the one hand, tetraalkylammonium chlorides such as, for example, dialkyldimethylammonium chlorides or alkyltrimethylammonium chlorides, in which the alkyl radical contains from about 12 to 22 carbon atoms, in particular behenyltrimethylammonium chloride, distearyldimethylammonium chloride, cetyltrimethylammonium chloride, or benzyldimethylstearylammonium chloride, or, on the other hand, palmitylamidopropyltrimethylammonium chloride or stearamido-propyldimethyl(myristyl acetate)ammonium chloride sold under the name Ceraphyl 70 by the company Van Dyk.

The fatty alcohols may be chosen from linear or branched $C_8$-$C_{22}$ fatty alcohols.

More particularly, the fatty alcohols are chosen from lauryl alcohol, myristyl alcohol, cetyl alcohol, stearyl alcohol, oleyl alcohol, isostearyl alcohol, isocetyl alcohol and oleyl alcohol, and mixtures thereof.

The fatty acids are chosen more particularly from myristic acid, palmitic acid, stearic acid, behenic acid, oleic acid, linoleic acid, linolenic acid and isostearic acid.

The fatty alcohol or fatty acid derivatives are especially carboxylic acid esters, in particular mono-, di-, tri- or tetracarboxylic esters.

The monocarboxylic acid esters are, in particular, linear or branched, saturated or unsaturated $C_1$-$C_{26}$ aliphatic acid monoesters of linear or branched, saturated or unsaturated, $C_1$-$C_{26}$ aliphatic alcohols, the total carbon number of these esters being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate.

$C_4$-$C_{22}$ di- or tricarboxylic acid esters of $C_1$-$C_{22}$ alcohols and mono-, di- or tricarboxylic acid esters of $C_2$-$C_{26}$ di-, tri-, tetra- or pentahydroxy alcohols can also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecylstearoyl stearate; pentaerythrityl monoricinoleate; pentaerythrityl tetrasononanoate; pentaerythrityl tetrapelargonate; pentaerythrityl tetraisostearate; pentaerythrityl tetraoctanoate; propylene glycol dicaprylate dicaprate; tridecyl erucate; triisopropyl citrate; triisostearyl citrate; glyceryl trilactate; glyceryl trioctanoate; trioctyldodecyl citrate; trioleyl citrate.

Among the esters mentioned above, it is preferred to use ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate and cetyl octanoate.

The fluoro oils are, for example, the perfluoropolyethers described in particular in patent application EP-A-486 135 and the fluorohydrocarbon compounds described in particular in patent application WO 93/11103. The teaching of these two patent applications is included in its entirety in the present application by way of reference.

The term "fluorohydrocarbon compounds" denotes compounds whose chemical structure contains a carbon skeleton in which certain hydrogen atoms have been replaced with fluorine atoms.

The fluoro oils can also be fluorocarbons such as fluoroamines, for example perfluorotributylamine, fluorohydrocarbons, for example perfluorodecahydronaphthalene, fluoro esters and fluoro ethers.

The perfluoropolyethers are sold, for example, under the trade names Fomblin by the company Montefluos and Krytox by the company Du Pont.

Among the fluorohydrocarbon compounds, mention may also be made of fluorine-containing fatty acid esters such as the product sold under the name Nofable FO by the company Nippon Oil.

Needless to say, it is possible to use mixtures of conditioners.

According to the invention, the conditioner(s) may represent from 0.001% to 20% by weight, preferably from 0.01% to 10% by weight and more particularly from 0.1% to 3% by weight, relative to the total weight of the final composition.

The compositions of the invention also advantageously contain at least one surfactant, which is generally present in an amount of between 0.1% and 60% by weight approximately, preferably between 1% and 40% and even more preferably between 5% and 30%, relative to the total weight of the composition.

This surfactant may be chosen from anionic, amphoteric and nonionic surfactants, or mixtures thereof.

The surfactants that are suitable for carrying out the present invention are especially the following:

(i) Anionic Surfactant(s):

In the context of the present invention, their nature does not represent a truly critical factor.

Thus, as examples of anionic surfactants which can be used, alone or as mixtures, in the context of the present invention, mention may be made in particular (nonlimiting list) of salts (in particular alkaline salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates and N-acyltaurates, the alkyl or acyl radical of all of these various compounds preferably containing from 8 to 24 carbon atoms, and the aryl radical preferably denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, in particular those containing from 2 to 50 ethylene oxide groups, and mixtures thereof.

Among the anionic surfactants, it is preferred according to the invention to use alkyl sulfate salts and alkyl ether sulfate salts and mixtures thereof.

(ii) Nonionic Surfactant(s):

The nonionic surfactants are, themselves also, compounds that are well known per se (see in particular in this respect "Handbook of Surfactants" by M. R. Porter, published by Blackie & Son (Glasgow and London), 1991, pp. 116-178) and, in the context of the present invention, their nature is not a critical feature. Thus, they can be chosen in particular from (nonlimiting list) polyethoxylated, polypropoxylated or polyglycerolated fatty acids, alkylphenols, α-diols or alcohols having a fatty chain containing, for example, 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides. It will be noted that the alkylpolyglycosides constitute nonionic surfactants that are particularly suitable in the context of the present invention.

(iii) Amphoteric Surfactant(s):

The amphoteric surfactants, whose nature is not a critical feature in the context of the present invention, can be, in particular (nonlimiting list), aliphatic secondary or tertiary amine derivatives in which the aliphatic radical is a linear or branched chain containing 8 to 22 carbon atoms and containing at least one water-soluble anionic group (for example carboxylate, sulfonate, sulfate, phosphate or phosphonate); mention may also be made of ($C_8$-$C_{20}$)alkylbetaines, sulfobetaines, ($C_8$-$C_{20}$)alkylamido($C_1$-$C_6$)alkylbetaines or ($C_8$-$C_{20}$)alkylamido($C_1$-$C_6$)alkylsulfobetaines.

Among the amine derivatives, mention may be made of the products sold under the name Miranol, as described in U.S. Pat. Nos. 2,528,378 and 2,781,354 and having the structures:

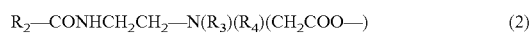

$$R_2-CONHCH_2CH_2-N(R_3)(R_4)(CH_2COO-) \quad (2)$$

in which: $R_2$ denotes an alkyl radical derived from an acid $R_2$—COOH present in hydrolyzed coconut oil, a heptyl, nonyl or undecyl radical, $R_3$ denotes a β-hydroxyethyl group and $R_4$ denotes a carboxymethyl group;

and

$$R_5-CONHCH_2CH_2-N(B)(C) \quad (3)$$

in which:

B represents —$CH_2CH_2OX'$, C represents —$(CH_2)_z$—Y', with z=1 or 2,

X' denotes the —$CH_2CH_2$—COOH group or a hydrogen atom,

Y' denotes —COOH or the —$CH_2$—CHOH—$SO_3H$ radical, $R_5$ denotes an alkyl radical of an acid $R_9$—COOH present in coconut oil or in hydrolyzed linseed oil, an alkyl radical, in particular a $C_7$, $C_9$, $C_{11}$ or $C_{13}$ alkyl radical, a $C_{17}$ alkyl radical and its iso form, an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caprylloamphodipropionate, lauroamphodipropionic acid, cocoamphodipropionic acid.

By way of example, mention may be made of the cocoamphodiacetate sold under the trade name Miranol C2M concentrate by the company Rhône-Poulenc.

In the compositions in accordance with the invention, mixtures of surfactants are preferably used, and in particular mixtures of anionic surfactants and mixtures of anionic surfactants and of amphoteric or nonionic surfactants. One mixture that is particularly preferred is a mixture consisting of at least one anionic surfactant and of at least one amphoteric surfactant.

The anionic surfactants preferably used are chosen from sodium, triethanolamine or ammonium ($C_{12}$-$C_{14}$)alkyl sulfates, sodium, triethanolamine or ammonium ($C_{12}$-$C_{14}$)alkyl ether sulfates oxyethylenated with 2.2 mol of ethylene oxide, sodium cocoyl isethionate and sodium α-($C_{14}$-$C_{16}$)olefin sulfonate, and mixtures thereof, with:

either an amphoteric surfactant such as the amine derivatives known as disodium cocoamphodipropionate or sodium cocoamphopropionate sold especially by the company Rhône-Poulenc under the trade name Miranol C2M CONC as an aqueous solution containing 38% active material, or under the name Miranol C32;

or an amphoteric surfactant of zwitterionic type such as alkylbetaines, in particular the cocobetaine sold under the name Dehyton AB 30 as an aqueous solution containing 32% AM by the company Henkel.

The composition of the invention may also contain at least one additive chosen from thickeners, fragrances, nacreous agents, preserving agents, anionic or nonionic polymers, non-cationic proteins, noncationic protein hydrolyzates, 18-methyleicosanoic acid, hydroxy acids, associative polymers other than those of the invention and in particular polyether nonionic associative polyurethanes, and any other additive conventionally used in cosmetics that does not affect the properties of the compositions according to the invention.

These additives are present in the composition according to the invention in proportions that may range from 0 to 20% by weight relative to the total weight of the composition. The precise amount of each additive is readily determined by a person skilled in the art, depending on its nature and its function.

The compositions in accordance with the invention may be used more particularly for washing or treating keratin materials such as the hair, the skin, the eyelashes, the eyebrows, the nails, the lips or the scalp, and more particularly the hair.

In particular, the compositions according to the invention are detergent compositions such as shampoos, shower gels and bubble baths. In this embodiment of the invention, the compositions comprise at least one washing base, which is generally aqueous.

The surfactant(s) forming the washing base may be chosen, without discrimination, alone or as mixtures, from the anionic, amphoteric and nonionic surfactants as defined above.

The quantity and quality of the washing base are those that are sufficient to give the final composition satisfactory foaming power and/or detergent power.

Thus, according to the invention, the washing base can represent from 4% to 50% by weight, preferably from 6% to 35% by weight and even more preferably from 8% to 25% by weight, relative to the total weight of the final composition.

The pH of the composition applied to the keratin materials is generally between 2 and 11. It is preferably between 3 and 8, and may be adjusted to the desired value by means of acidifying or basifying agents that are well known in the prior art for compositions applied to keratin fibers.

Among the basifying agents that may be mentioned, for example, are aqueous ammonia, alkali metal carbonates, alkanolamines such as monoethanolamine, diethanolamine and triethanolamine and also derivatives thereof, oxyethylenated and/or oxypropylenated hydroxyalkylamines and ethylenediamines, sodium hydroxide, potassium hydroxide and the compounds of formula (XIX) below:

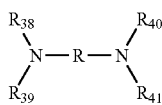

(XIX)

in which R is a propylene residue optionally substituted with a hydroxyl group or a $C_1$-$C_4$ alkyl radical; $R_{38}$, $R_{39}$, $R_{40}$ and $R_{41}$, which may be identical or different, represent a hydrogen atom, a $C_1$-$C_4$ alkyl radical or a $C_1$-$C_4$ hydroxyalkyl radical.

The acidifying agents are conventionally, for example, mineral or organic acids, for instance hydrochloric acid, orthophosphoric acid, carboxylic acids, for instance tartaric acid, citric acid or lactic acid, or sulfonic acids.

The physiologically and in particular cosmetically acceptable medium may consist solely of water, of a cosmetically acceptable solvent or of a mixture of water and a cosmetically acceptable solvent such as, especially, a $C_1$-$C_4$ lower alcohol, for instance ethanol, isopropanol, tert-butanol or n-butanol; alkylene glycols, for instance propylene glycol, and glycol ethers.

A subject of the invention is also a process for treating keratin materials such as the skin or the hair, characterized in that it consists in applying to the keratin materials a cosmetic composition as defined above, optionally followed by rinsing with water.

Thus, this process according to the invention allows holding of the hairstyle and the treatment, care and washing of or removal of makeup from the skin, the hair or any other keratin material.

The compositions of the invention may also be in the form of a rinse-out or leave-in conditioner, permanent-waving, hair-straightening, dyeing or bleaching compositions, or alternatively in the form of rinse-out compositions to be applied before or after dyeing, bleaching, permanent-waving or straightening the hair, or alternatively between the two steps of a permanent-waving or hair-straightening operation.

The compositions of the invention may also be in the form of washing compositions for the skin, in particular in the form of bath or shower solutions or gels or makeup-removing products.

The compositions according to the invention may also be in the form of aqueous or aqueous-alcoholic lotions for skincare and/or haircare.

The cosmetic compositions according to the invention may be in the form of a gel, a milk, a cream, an emulsion, a thickened lotion or a mousse and may be used for the skin, the nails, the eyelashes, the lips and, more particularly, the hair.

The compositions may be packaged in various forms, especially in vaporizers, pump-dispenser bottles or in aerosol containers to allow the composition to be applied in vaporized form or in the form of a mousse. Such packaging forms are indicated, for example, when it is desired to obtain a spray, a lacquer or a mousse for treating the hair.

Throughout the text hereinabove and hereinbelow, the percentages expressed are on a weight basis.

The invention will now be illustrated more fully with the aid of the examples that follow, which cannot be considered as limiting it to the embodiments described.

EXAMPLES

In the examples, AM means active material.
Polymer 1 is the following polymer:

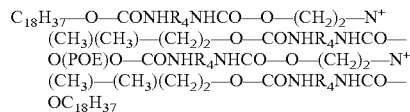

with:
counterion: $CH_3SO_4^-$
$R_4$=methylenedicyclohexyl.

0.01 mol of PEG 150+0.0006 mol of tin 2-ethylhexanoate+ 100 ml of tetrahydrofuran (THF) are introduced into a 500 ml reactor with central mechanical stirring, thermometer, condenser and introduction of nitrogen.

The mixture is stirred at room temperature to obtain a homogeneous solution, followed by dropwise addition of 0.02 mol of methylenedicyclohexyl 4,4'-diisocyanate while remaining at room temperature.

The mixture is then heated to the reflux point of the solvent (66° C.) over 30 minutes and is left at this temperature for about 15 hours.

0.02 mol of N-methyldiethanolamine is then introduced and is left to react for two hours at 66° C. (the disappearance of the CNO band of the isocyanate is monitored by IR), followed by addition of 0.02 mol of methylenedicyclohexyl 4,4'-diisocyanate, which is left to react for three hours (the disappearance of the CNO band of the isocyanate is monitored by IR) and finally 0.02 mol of octadecanol.

The mixture is left for a further three hours at the reflux point of the solvent.

The polymer is then quaternized with 0.022 mol of dimethyl sulfate.

The reaction medium opacifies, and heating is maintained at 66° C. for 48 hours.

The mixture is cooled to room temperature.

The polyurethane is purified by precipitation from petroleum ether, filtered off and dried under vacuum at 55° C. to constant weight.

The final product is in the form of a white powder.
The yield is 88%.
Polymer 2 is the following polymer:

$C_{18}H_{37}N^+(CH_3)(CH_3)$—$(CH_2)_2$—O—
CONHR$_4$NHCO—O(POE)O—
CONHR$_4$NHCO—O—$(CH_2)_2$—$N^+(CH_3)(CH_3)$
$C_{18}H_{37}$ with:
R$_4$=methylenedicyclohexyl
counterion: Br$^-$.

0.01 mol of PEG 150+0.0006 mol of tin 2-ethylhexanoate+ 100 ml of tetrahydrofuran (THF) are introduced into a 500 ml reactor with central mechanical stirring, thermometer, condenser and introduction of nitrogen.

The mixture is stirred at room temperature to obtain a homogeneous solution, followed by dropwise addition of 0.02 mol of methylenedicyclohexyl 4,4'-diisocyanate while remaining at room temperature (the disappearance of the CNO band of the isocyanate is monitored by IR).

0.02 mol of N,N-dimethylethanolamine is then added and the mixture is left at 66° C. for four hours.

The polymer is then quaternized with 0.024 mol of stearyl bromide.

Heating is then continued at 66° C. for 24 hours.

The mixture is cooled to room temperature.

The polyurethane is purified by precipitation from petroleum ether, filtered off and dried under vacuum at 55° C. to constant weight.

The final product is in the form of a white powder.
The yield is 92%.

Example 1

A shampoo composition was prepared:

| | |
|---|---|
| Sodium lauryl ether sulfate containing 2.2 mol of ethylene oxide, at 28% AM | 17 g AM |
| Cocoylbetaine at 30% AM | 2.5 g AM |
| Polymer 1 | 1 g AM |
| Coconut acid monoisopropanolamide | 0.6 g |
| 2-hydroxy-4-methoxybenzophenone-5-sulfonic acid (Uvinul MS 40 from BASF) | 0.1 g |
| Fragrance, preserving agents | qs |
| Demineralized water qs | 100 g |

Hair treated with this shampoo is smooth, soft and protected against the harmful action of light.

Example 2

The following shampoo composition was prepared:

| | |
|---|---|
| Sodium lauryl ether sulfate containing 2.2 mol of ethylene oxide, at 30% AM | 10 g AM |
| Cocoylbetaine at 30% AM | 4 g AM |
| Polymer 2 | 0.5 g AM |
| Polydimethylsiloxane of viscosity 300 000 cSt (Silicone AK300 000 from Wacker) | 0.5 g |
| Xanthan gum | 1 g |
| Citric acid qs pH | 7 |
| Demineralized water qs | 100 g |

Hair treated with this shampoo is smooth and soft.

Example 3

A conditioner in accordance with the invention, having the composition below, was prepared:

| | |
|---|---|
| Polymer 1 | 0.5 g AM |
| Behenyltrimethylammonium chloride | 1.5 g AM |
| Mixture of cetylstearyl alcohol and of cetylstearyl alcohol oxyethylenated with 33 EO (80/20) | 4 g |
| Demineralized water qs | 100 g |

Example 4

A conditioner in accordance with the invention, having the composition below, was prepared:

| | |
|---|---|
| Polymer 2 | 0.5 g AM |
| Behenyltrimethylammonium chloride | 1.5 g AM |
| N-Oleoyldihydrosphingosine | 0.5 g |
| Water qs | 100 g |

The invention claimed is:

1. A composition for treating a keratin material comprising, in a physiologically acceptable medium,
at least one agent chosen from protecting agents and conditioning agents and at least one cationic associative polyurethane of formula (I):

R—X—(P)$_n$-[L-(Y)$_m$]$_r$-L'-(P')$_p$—X'—R'   (I)

wherein:
R and R', which may be identical or different, are each chosen from; saturated and unsaturated, linear and branched C$_{10}$-C$_{30}$ hydrocarbon-based chains;
X and X', which are identical, are chosen from groups L" and groups of the following formulae:

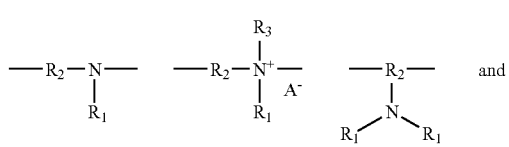 and

-continued

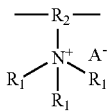

wherein:
  $R_2$ is chosen from linear and branched $C_1$-$C_{20}$ alkylene radicals;
  $R_1$ and $R_3$, which may be identical or different, are each chosen from linear and branched $C_1$-$C_{30}$ alkyl radicals; and
  $A^-$ is chosen from physiologically acceptable counterions;
L, L' and L'', which may be identical or different, are each chosen from groups of the following formula:

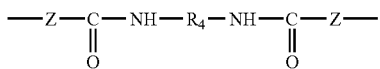

wherein:
  Z is chosen from —O—, —S— and —NH—; and
  $R_4$ is chosen from linear and branched $C_1$-$C_{20}$ alkylene radicals, methylenediphenyl, methylenedicyclohexyl, isophorone, and arylene radicals chosen from toluene and naphthalene;
P and P', which may be identical or different, are each chosen from groups of the following formulae:

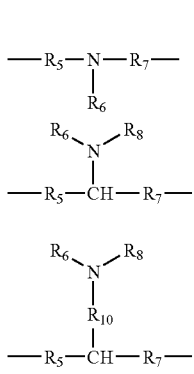

wherein:
  $R_5$ and $R_7$, which may be identical or different, are each chosen from linear and branched $C_1$-$C_{20}$ alkylene radicals;
  $R_6$, $R_8$ and $R_9$, which may be identical or different, are each chosen from linear and branched $C_1$-$C_{30}$ alkyl radicals;
  $R_{10}$ is chosen from linear and branched, optionally unsaturated alkylene groups, and
  $A^-$ is chosen from physiologically acceptable counterions;
Y is chosen from groups derived from ethylene glycol, diethylene glycol, and propylene glycol, and groups derived from a polymer chosen from polyethers chosen from poly(ethylene oxide) and poly(propylene oxide);
r is an integer ranging from 1 to 100;
n, m and p, which may be identical or different, each range from 0 to 1000;
with the exclusion of the following compositions:
  (1) compositions for direct dyeing of keratin fibers, comprising, in a medium suitable for dyeing, at least one direct dye and at least one cationic associative polyurethane of formula (I),
  (2) compositions for oxidation dyeing of keratin fibers, comprising, in a medium suitable for dyeing, at least one oxidation dye and at least one cationic associative polyurethane of formula (I),
  (3) ready-to-use compositions for bleaching keratin fibers, comprising, in a medium suitable for bleaching, at least one oxidizing agent and at least one cationic associative polyurethane of formula (I), and
  (4) ready-to-use compositions for bleaching or permanently reshaping keratin fibers, comprising, in a medium suitable for bleaching, at least one reducing agent and at least one cationic associative polyurethane of formula (I).

2. The composition according to claim 1, wherein the keratin material is human keratin fibers.

3. The composition according to claim 2, wherein the human keratin fibers are hair.

4. The composition according to claim 1, wherein the physiologically acceptable medium is a cosmetically acceptable medium.

5. The composition according to claim 1, wherein, in formula (I), r is an integer ranging from 1 to 50.

6. The composition according to claim 5, wherein, in formula (I), r is an integer ranging from 1 to 25.

7. The composition according to claim 1, wherein
  X and X', which are identical, are chosen from groups L'', and
  n and p, which may be identical or different, each range from 1 to 1000.

8. The composition according to claim 1, wherein
  X and X', which are identical, are chosen from groups L'', and
  n and p are 0.

9. The composition according to claim 1, wherein
  R and R', which may be identical or different, are each chosen from saturated and unsaturated, linear and branched $C_{10}$-$C_{30}$ hydrocarbon-based chains;
  X and X', which are identical, are chosen from groups

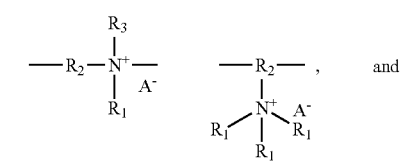

n and p are zero.

10. The composition according to claim 1, wherein the at least one cationic associative polyurethane has a number-average molecular mass ranging from 400 to 500 000.

11. The composition according to claim 10, wherein the at least one cationic associative polyurethane has a number-average molecular mass ranging from 1000 to 400 000.

12. The composition according to claim 11, wherein the at least one cationic associative polyurethane has an number-average molecular mass ranging from 1000 to 300 000.

13. The composition according to claim 1, wherein the at least one cationic associative polyurethane is present in an amount ranging from 0.01% to 10% by weight, relative to the total weight of the composition.

14. The composition according to claim 13, wherein the at least one cationic associative polyurethane is present in an amount ranging from 0.1% to 5% by weight, relative to the total weight of the composition.

15. The composition according to claim 1, wherein the protecting agents are chosen from UV-screening agents, free-radical scavengers, antioxidants, vitamins, provitamins, and sequestering agents.

16. The composition according to claim 15, wherein the UV-screening agents are chosen from water-soluble screening agents, liposoluble screening agents, silicone screening agents, nonsilicone screening agents, and mineral oxide nanoparticles whose surface has optionally been treated to make them hydrophilic or hydrophobic.

17. The composition according to claim 16, wherein the water-soluble UV-screening agents are chosen from at least one of para-aminobenzoic acid and salts thereof, anthranilic acid and salts thereof, salicylic acid and salts thereof, p-hydroxycinnamic acid and salts thereof, sulfonic derivatives of benz-x-azoles and salts thereof, sulfonic derivatives of benzophenone and salts thereof, sulfonic derivatives of benzylidenecamphor and salts thereof, benzylidenecamphor derivatives substituted with at least one quaternary amine and salts thereof, phthalylidene-camphorsulfonic acid derivatives and salts thereof, sulfonic derivatives of benzotriazole and salts thereof, and hydrophilic polymers having at least one UV-photoprotective property.

18. The composition according to claim 16, wherein the liposoluble UV-screening agents are chosen from at least one of p-aminobenzoic acid derivatives; salicylic acid derivatives; benzophenone derivatives; dibenzoylmethane derivatives; diphenylacrylate derivatives; benzofuran derivatives; polymeric UV-screening agents comprising at least one organosilicon residue; cinnamic acid esters; camphor derivatives; trianilino-s-triazine derivatives; urocanic acid ethyl ester; benzotriazoles; hydroxyphenyltriazine derivatives; and bis-resorcinol-dialkylaminotriazines.

19. The composition according to claim 18, wherein the p-aminobenzoic acid derivatives are chosen from p-aminobenzoic acid esters and p-aminobenzoic acid amides.

20. The composition according to claim 18, wherein the salicylic acid derivatives are chosen from esters of salicylic acids.

21. The composition according to claim 16, wherein the liposoluble UV-screening agents are chosen from octyl salicylate; 2-hydroxy-4-methoxybenzophenone; 4-tert-butyl-4'-methoxydibenzoylmethane; octocrylene; 2-ethylhexyl 4-methoxycinnamate; and the compound of formula (II):

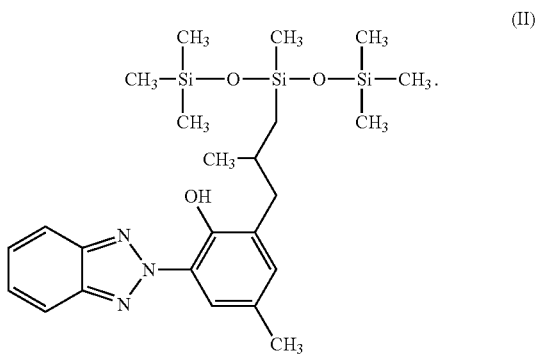

22. The composition according to claim 1, wherein the conditioning agents are chosen from at least one of synthetic oils, mineral oils, plant oils, fluoro oils, perfluoro oils, natural waxes, synthetic waxes, silicones, cationic polymers, ceramide compounds, cationic surfactants, fatty amines, fatty acids and derivatives thereof, and fatty alcohols and derivatives thereof.

23. The composition according to claim 22, wherein the synthetic oils are chosen from polyolefins of hydrogenated and nonhydrogenated polybutene type, and polyolefins of hydrogenated and nonhydrogenated polydecene type.

24. The composition according to claim 22, wherein the cationic polymers are chosen from polymers comprising units comprising at least one group chosen from primary, secondary, tertiary and quaternary amine groups that may either form part of the main polymer chain or may be borne by a side substituent directly attached to the main polymer chain.

25. The composition according to claim 22, wherein the cationic polymers are chosen from at least one of quaternary cellulose ether derivatives, cationic cyclopolymers, cationic polysaccharides, and quaternary polymers of vinylpyrrolidone and of vinylimidazole.

26. The composition according to claim 25, wherein the cationic cyclopolymers are chosen from diallyldimethylammonium chloride homopolymers, and copolymers of diallyldimethylammonium chloride and of acrylamide.

27. The composition according to claim 25, wherein the quaternary cellulose ether derivatives are chosen from hydroxyethylcelluloses that have reacted with an epoxide substituted with at least one trimethylammonium group.

28. The composition according to claim 25, wherein the cationic polysaccharides are chosen from guar gums modified with a 2,3-epoxypropyltrimethylammonium salt.

29. The composition according to claim 22, wherein the silicones are chosen from polyorganosiloxanes that are insoluble in the composition.

30. The composition according to claim 29, wherein the polyorganosiloxanes are chosen from nonvolatile polyorganosiloxanes chosen from at least one of polyalkylsiloxanes, polyarylsiloxanes, polyalkylarylsiloxanes, silicone gums, silicone resins, and polyorganosiloxanes modified with at least one organofunctional group.

31. The composition according to claim 30, wherein
   (a) the polyalkylsiloxanes are chosen from:
   polydimethylsiloxanes comprising trimethylsilyl end groups;
   polydimethylsiloxanes comprising dimethylsilanol end groups; and
   poly($C_1$-$C_{20}$)alkylsiloxanes;
   (b) the polyalkylarylsiloxanes are chosen from:
   linear and branched polydimethylmethylphenylsiloxanes and linear and branched polydimethyldiphenylsiloxanes with a viscosity ranging from $1\times10^{-5}$ to $5\times10^{-2}$ m$^2$/s at 25° C.;
   (c) the silicone gums are chosen from polydiorganosiloxanes with number-average molecular masses ranging from 200 000 to 1 000 000, used alone or in the form of a mixture in at least one solvent;
   (d) the silicone resins are chosen from resins comprising at least one unit chosen from units of $(R'')_3SiO_{1/2}$, $(R'')_2SiO_{2/2}$, $R''SiO_{3/2}$ and $SiO_{4/2}$,
   wherein R'' is chosen from hydrocarbon-based groups comprising from 1 to 16 carbon atoms and a phenyl group;
   (e) the organomodified silicones are chosen from silicones comprising at least one organofunctional group attached via a hydrocarbon-based radical.

32. The composition according to claim 31, wherein the silicone gums are chosen from:
- polydimethylsiloxane, polydimethylsiloxane/methylvinylsiloxanes,
- polydimethylsiloxane/diphenylsiloxane,
- polydimethylsiloxane/phenylmethylsiloxane,
- polydimethylsiloxane/diphenylsiloxane/methylvinylsiloxanes, and the following mixtures:
  - mixtures formed from a polydimethylsiloxane hydroxylated at the chain end and from a cyclic polydimethylsiloxane;
  - mixtures formed from a polydimethylsiloxane gum and from a cyclic silicone; and
  - mixtures of polydimethylsiloxanes of different viscosities.

33. The composition according to claim 31, wherein the organomodified silicones are chosen from polyorganosiloxanes comprising at least one group chosen from:
- a) polyethyleneoxy and polypropyleneoxy groups;
- b) substituted and unsubstituted amine groups;
- c) thiol groups;
- d) alkoxylated groups;
- e) hydroxyalkyl groups;
- f) acyloxyalkyl groups;
- g) alkylcarboxylic groups;
- h) 2-hydroxyalkyl sulfonate groups;
- i) 2-hydroxyalkyl thiosulfonate groups; and
- j) hydroxyacylamino groups.

34. The composition according to claim 29, wherein the polyorganosiloxanes are chosen from polyalkylsiloxanes comprising trimethylsilyl end groups, polyalkylsiloxanes comprising dimethylsilanol end groups, polyalkylarylsiloxanes, mixtures of two PDMSs comprising a gum and an oil of different viscosities, mixtures of organosiloxanes and of cyclic silicones, and organopolysiloxane resins.

35. The composition according to claim 22, wherein the ceramide compounds are chosen from at least one of:
- 2-N-linoleoylaminooctadecane-1,3-diol,
- 2-N-oleoylaminooctadecane-1,3-diol,
- 2-N-palmitoylaminooctadecane-1,3-diol,
- 2-N-stearoylaminooctadecane-1,3-diol,
- 2-N-behenoylaminooctadecane-1,3-diol,
- 2-N-[2-hydroxypalmitoyl]aminooctadecane-1,3-diol,
- 2-N-stearoylaminooctadecane-1,3,4-triol,
- 2-N-palmitoylaminohexadecane-1,3-diol,
- bis(N-hydroxyethyl-N-cetyl)malonamide,
- N-(2-hydroxyethyl)-N-(3-cetyloxy-2-hydroxypropyl) cetylamide, and
- N-docosanoyl-N-methyl-D-glucamine.

36. The composition according to claim 35, wherein the 2-N-stearoylaminooctadecane-1,3,4-triol is chosen from N-stearoylphytosphingosine.

37. The composition according to claim 1, wherein the at least one agent chosen from protecting agents and conditioning agents is present in an amount ranging from 0.001% to 20% by weight, relative to the total weight of the composition.

38. The composition according to claim 37, wherein the at least one agent chosen from protecting agents and conditioning agents is present in an amount ranging from 0.01% to 10% by weight, relative to the total weight of the composition.

39. The composition according to claim 1, further comprising at least one surfactant chosen from anionic, nonionic and amphoteric surfactants.

40. The composition according to claim 39, wherein the at least one surfactant is present in an amount ranging from 0.1% to 60% by weight, relative to the total weight of the composition.

41. The composition according to claim 40, wherein the at least one surfactant is present in an amount ranging from 1% to 40% by weight, relative to the total weight of the composition.

42. The composition according to claim 41, wherein the at least one surfactant is present in an amount ranging from 5% to 30% by weight, relative to the total weight of the composition.

43. The composition according to claim 1, wherein the composition is in a form chosen from shampoos, conditioners, compositions for permanent-waving hair, compositions for straightening hair, compositions for dyeing hair, compositions for bleaching hair, rinse-out compositions to be applied between the two steps of a permanent-waving operation and a hair-straightening operation, and washing compositions for the body.

* * * * *